US009744174B2

(12) United States Patent
Friedhoff

(10) Patent No.: US 9,744,174 B2
(45) Date of Patent: Aug. 29, 2017

(54) METHOD FOR NORIBOGAINE TREATMENT IN PATIENTS ON METHADONE

(71) Applicant: DemeRx, Inc., Fort Lauderdale, FL (US)

(72) Inventor: Lawrence Friedhoff, River Vale, NJ (US)

(73) Assignee: DEMERX, INC., Fort Lauderdale, FL (US)

( * ) Notice: Subject to any disclaimer, the term of this patent is extended or adjusted under 35 U.S.C. 154(b) by 0 days.

(21) Appl. No.: 14/295,273

(22) Filed: Jun. 3, 2014

(65) Prior Publication Data

US 2015/0045350 A1   Feb. 12, 2015

Related U.S. Application Data

(63) Continuation-in-part of application No. PCT/US2013/069235, filed on Nov. 8, 2013.

(60) Provisional application No. 61/852,485, filed on Mar. 15, 2013.

(51) Int. Cl.
A61K 31/137 (2006.01)
A61K 31/55 (2006.01)

(52) U.S. Cl.
CPC ............ *A61K 31/55* (2013.01); *A61K 31/137* (2013.01)

(58) Field of Classification Search
None
See application file for complete search history.

(56) References Cited

U.S. PATENT DOCUMENTS

| | | | |
|---|---|---|---|
| 2,817,623 | A | 12/1957 | Schneider |
| 4,626,539 | A | 12/1986 | Aungst et al. |
| 4,806,341 | A | 2/1989 | Chien et al. |
| 5,149,538 | A | 9/1992 | Granger et al. |
| 5,591,738 | A | 1/1997 | Lotsof |
| 5,616,575 | A | 4/1997 | Efange et al. |
| 6,348,456 | B1 | 2/2002 | Mash et al. |
| 6,416,793 | B1 | 7/2002 | Zeligs et al. |
| 6,933,308 | B2 | 8/2005 | Boy et al. |
| 7,220,737 | B1 | 5/2007 | Mash |
| 7,754,710 | B2 | 7/2010 | Mash |
| 8,178,524 | B2 | 5/2012 | Mash |
| 8,362,007 | B1 | 1/2013 | Mash et al. |
| 8,637,648 | B1 | 1/2014 | Mash et al. |
| 8,648,198 | B2 | 2/2014 | Furukawa et al. |
| 8,741,891 | B1 | 6/2014 | Mash |
| 8,742,096 | B2 | 6/2014 | Moriarty et al. |
| 8,765,737 | B1 | 7/2014 | Mash et al. |
| 8,853,201 | B2 | 10/2014 | Gless et al. |
| 8,940,728 | B2 | 1/2015 | Mash et al. |
| 9,045,481 | B2 | 6/2015 | Mash et al. |
| 9,308,272 | B2 | 4/2016 | Mash et al. |
| 2003/0153552 | A1 | 8/2003 | Mash et al. |
| 2003/0194438 | A1 | 10/2003 | Prescott et al. |
| 2006/0229293 | A1 | 10/2006 | Lotsof |
| 2007/0185085 | A1 | 8/2007 | Mash |
| 2010/0311722 | A1 | 12/2010 | Mash |
| 2010/0311723 | A1 | 12/2010 | Mash |
| 2010/0311725 | A1 | 12/2010 | Mash |
| 2012/0083485 | A1 | 4/2012 | Mash |
| 2013/0011444 | A1 | 1/2013 | Zebala |
| 2013/0072472 | A1 | 3/2013 | Gless et al. |
| 2013/0131046 | A1 | 5/2013 | Moriarty et al. |
| 2013/0165414 | A1 | 6/2013 | Gless et al. |
| 2013/0165425 | A1 | 6/2013 | Gless et al. |
| 2013/0165647 | A1 | 6/2013 | Moriarty et al. |
| 2013/0211073 | A1 | 8/2013 | Moriarty |
| 2013/0211074 | A1 | 8/2013 | Moriarty |
| 2013/0296823 | A1 | 11/2013 | Melker et al. |
| 2013/0303756 | A1 | 11/2013 | Mash et al. |
| 2014/0179685 | A1 | 6/2014 | Mash et al. |
| 2014/0288056 | A1 | 9/2014 | Friedhoff |
| 2014/0315891 | A1 | 10/2014 | Mash |
| 2014/0357741 | A1 | 12/2014 | Mash et al. |
| 2015/0045350 | A1 | 2/2015 | Friedhoff |
| 2015/0231145 | A1 | 8/2015 | Friedhoff |
| 2015/0231146 | A1 | 8/2015 | Friedhoff |
| 2015/0238503 | A1 | 8/2015 | Maillet et al. |

(Continued)

FOREIGN PATENT DOCUMENTS

| WO | WO-96/03127 A1 | 2/1996 |
|---|---|---|
| WO | WO 99/11250 | 3/1999 |

(Continued)

OTHER PUBLICATIONS

"Methadone-induced Torsade de pointes tachycardias" by Sticherling et al., Swiss Med. Weekly 135, 282-85 (2005).*
Breen et al., Drug Alcohol Depend. 71, 49-55 (2003).*
Mash et al., Ann. NY Acad. Sci. 914, 394-401 (2000).*
U.S. Appl. No. 13/104,406, filed May 10, 2011, Mash et al.
U.S. Appl. No. 14/298,534, filed Jun. 6, 2014, Mash et al.
U.S. Appl. No. 14/195,822, filed Mar. 3, 2014, Friedhoff, Lawrence.
U.S. Appl. No. 14/292,632, filed May 30, 2014, Friedhoff, Lawrence.
Calsyn et al., "Slow tapering from methadone maintenance in a program encouraging indefinite maintenance," Journal of Substance Abuse Treatment, 2006, 30:159-163.

(Continued)

*Primary Examiner* — Theodore R West
(74) *Attorney, Agent, or Firm* — Foley & Lardner LLP

(57) ABSTRACT

A short treatment with noribogaine shows promise for treating drug dependency. Many opioid addicts are treated with methadone. Giving noribogaine to mammal concurrently being administered methadone surprisingly exacerbates methadone's negative side-effects, and increases the risk of death. Therefore, prior to noribogaine treatment, a patient on methadone therapy undergoes a period of methadone abstinence to wash out the methadone. Surprisingly, noribogaine does not react negatively to morphine. According to the invention, methadone regimen is replaced with morphine prior to noribogaine treatment.

23 Claims, 7 Drawing Sheets

(56) References Cited

U.S. PATENT DOCUMENTS

| | | |
|---|---|---|
| 2015/0246055 A1 | 9/2015 | Friedhoff |
| 2015/0257667 A1 | 9/2015 | Friedhoff |
| 2015/0258105 A1 | 9/2015 | Maillet et al. |
| 2015/0258106 A1 | 9/2015 | Friedhoff |
| 2015/0258107 A1 | 9/2015 | Friedhoff |
| 2015/0258108 A1 | 9/2015 | Maillet et al. |
| 2015/0258111 A1 | 9/2015 | Maillet et al. |
| 2015/0258113 A1 | 9/2015 | Friedhoff |
| 2015/0258114 A1 | 9/2015 | Friedhoff |
| 2015/0342959 A1 | 12/2015 | Friedhoff |
| 2016/0008372 A1 | 1/2016 | Weis |
| 2016/0038508 A1 | 2/2016 | Perry et al. |
| 2016/0220579 A1 | 8/2016 | Weis et al. |

FOREIGN PATENT DOCUMENTS

| | | |
|---|---|---|
| WO | WO-2012/012764 A1 | 1/2012 |
| WO | WO-2012/103028 | 8/2012 |
| WO | WO-2013/040471 | 3/2013 |
| WO | WO-2013/085849 A2 | 6/2013 |
| WO | WO-2013/085922 A1 | 6/2013 |
| WO | WO-2013/112622 | 8/2013 |
| WO | WO-2013/112673 | 8/2013 |
| WO | WO-2014/019692 | 2/2014 |
| WO | WO-2014/144508 | 9/2014 |
| WO | WO-2015/126434 | 8/2015 |
| WO | WO-2015/126836 | 8/2015 |
| WO | WO-2015/163844 | 10/2015 |
| WO | WO-2015/195673 | 12/2015 |
| WO | WO-2016/086194 | 6/2016 |
| WO | WO-2016/134019 | 8/2016 |

OTHER PUBLICATIONS

Donnelly, J.R., "The Need for Ibogaine in Drug and Alcohol Addiction Treatment," Journal of Legal Medicine, 2011, 32:93-114.
Eap et al., "Interindividual Variability of the Clinical Pharmacokinetics of Methadone," Clinical Pharmacokinetics, 2002, 41(14):1153-1193.
Huffman et al., "A Formal Synthesis of (±)-Ibogamine", J. Org. Chem., 1985, 50:1460.
Khan et al., "Long QT syndrome: Diagnosis and management", American Heart Journal, 2002, 143(1):7-14.
Mitchell et al., "Temperature and the cold pressor test", J. Pain, 2004, 5:233-237.
PCT International Search Report and Written Opinion for Appl. No. PCT/US13/69235, dated Mar. 10, 2014.
PCT International Search Report and Written Opinion for Appl. No. PCT/US2014/028946, dated Jul. 28, 2014.
Pearl et al., "Radioligand-binding Study of Noribogaine, A Likely Metabolite of Ibogaine", Brain Research, 1995, 675:342-344.
Weiss et al., "Neurobiology of craving, conditioned reward and relapse", Current Opinion in Pharmacology, 2005, 5:9-19.
Bhargava, et al., "Effects of noribogaine on the development of tolerance to antinociceptive action of morphine in mice," Brain Research, (1997) 771:343-346.
Bhargava, et al., "Effects of ibogaine and noribogaine on the antinociceptive action of μ-, σ- and κ-opioid receptor agonists in mice," Brain Research, (1997), 752:234-238.
Cao, et al., "Effects of ibogaine on the development of tolerance to antinociceptive action of μ-, σ- and κ-opioid receptor agonists in mice," Brain Research, (1997), 752:250-254.
International Search Report and Written Opinion Application No. PCT/US2015/062783, mail date Feb. 9, 2016, 16 pages.
Kroupa, et al., "Ibogaine in the 21st Century: Boosters, Tune-ups and Maintenance," MAPS, (2005), 15(1):21-24.
New Zealand Ministry of Health, Prescriber Update (2010), 31(4), pp. 27-29.
PCT International Preliminary Report on Patentability for PCT Patent Application No. PCT/US14/19692, dated Feb. 1, 2016. 19 pages.
Popik et. al. "100 Years of Ibogaine: Neourochemical and Pharmacological Actions of a Putative Anti-addictive Drug." Pharmacological Reviews (1995)47:235:253.
Sharma et. al. "Enhancement of Morphine Antinociception by Ibogaine and Noribogaine in Morphine-tolerant Mice," Pharmacology (1998) 57:229-232.
U.S. Appl. No. 13/593,454, filed Aug. 23, 2012, Moriarty et al.
Australian New Zealand Clinical Trials Registry ACTRN12612000821897, 2012.
International Preliminary Report on Patentability dated Sep. 24, 2015 for PCT Application No. PCT/US2014/028946.
International Preliminary Report on Patentability for PCT/US2013/069235, mailed Sep. 24, 2015.
Jaffe. "Drug Addiction and Drug Abuse", Goodman and Gilman's The Pharmacological Basis of Therapeutics, 8th Ed., date unknown, pp. 520-523 & pp. 559-568.
Krantz et al., "QTc Interval Screen in Methadone Treatment," Annals of Internal Medicine, 2009, American College of Physicians, vol. 150, pp. 387-395.
Kubiliene, et al., "Acute toxicity of ibogaine and noribogaine," Medicina (Kaunas), (2008), 44(12):984-988.
Maillet et al., "Noribogaine is a G-protein biased k-opioid receptor agonist", Neuropharmacology, 2015, 99, pp. 675-688.
PCT International Search Report and Written Opinion for Appl No. PCT/US2015/016186 dated Apr. 24, 2015 5 Pages.
PCT International Search Report and Written Opinion for Appl. No. PCT/US2014/019692 dated Nov. 18, 2014.
Zubaran et a., "Noribogaine Generalization to the Ibogaine Stimulus: Correlation with Noribogaine Concentration in Rat Brain", Neuropsychopharmacology, 1999, vol. 21, pp. 119-126.
International Search Report and Written Opinion for related application No. PCT/US2016/031932, dated Dec. 8, 2016.
Chang et al., "Noribogaine reduces nicotine self-administration in rats," Journal of Pyschopharmacology, May 20, 2015 (May 20, 2015), vol. 29, No. 6, pp. 704-711.
Cubeddu, "QT Prolongation and Fatal Arrhythmias: A Review of Clinical Implications and Effects of Drugs", American Journal of Therapeutics 10, pp. 452-457, 2003.
Fermini et al., "The Impact of Drug-Induced QT Interval Prolongation on Drug Discovery and Development", Nature Reviews Drug Discovery 2003, 2, 439-447.
Goutarel, et al., "Pharmacodynamics and Therapeutic Applications of Iboga and Ibogaine," Psychedelic Monographs and Essays, vol. 6:70-111, 1993.
Hoelen et al., "Long-QT Syndrome Induced by the Antiaddiction Drug Ibogaine," N Engl J Med, 360(3) pp. 308-309, Jan. 15, 2009.
Malik et al., "Evaluation of Drug-Induced QT Interval Prolongation," Drug Safety, 2001, 24(5), pp. 323-351.
International Search Report and Written Opinion for related PCT Patent Application No. PCT/US16/18273, dated Jun. 10, 2016.
Sala et al. "QT Interval Prolongation related to psychoactive drug treatment: a comparison of monotherapy versus polytherapy", Ann Gen Psychiatry 2005; 4(1):1.

* cited by examiner

METHOD FOR NORIBOGAINE TREATMENT IN PATIENTS ON METHADONE

PRIORITY

This application is a Continuation-in-Part of PCT Application No. PCT/US2013/069235 filed Nov. 8, 2013, which claims the benefit of U.S. Provisional Application No. 61/852,485, filed Mar. 15, 2013, entitled "METHOD FOR NON-TOXIC TREATMENT FOR DRUG WITHDRAWAL", each of which is incorporated herein in its entirety by reference as if fully set forth herein.

FIELD OF THE INVENTION

This invention relates to the administration of noribogaine for the treatment of addiction, and avoiding negative drug interactions. The invention is particularly relevant in the treatment of opioid addiction in human patients who are currently treated with methadone.

STATE OF THE ART

Current treatments for opiate drug dependency include replacing the addictive opiate with another, less-harmful drug that, in theory, is slowly tapered. Methadone, a synthetic opioid, is often used as an opioid replacement for the treatment of heroin addiction, in part because it is slowly metabolized and does not give a "high" associated with opioids. While methadone is effective for reducing illicit drug use in dependent individuals, methadone administration must be maintained indefinitely in these individuals to prevent relapse. In fact, studies have reported over 80% relapse in individuals that discontinued methadone maintenance treatment. Methadone is also addictive, in both patients who were previously addicted to opioids and for the millions who are prescribed methadone for the treatment of pain. Such addiction is often manifested by the desire of patients to increase the amount of methadone used over time.

The side effects of methadone include heart arrhythmia, and the risk of overdose when combined with other tranquilizers or when dosed too frequently, especially in view of the long-half-life of methadone, in vivo. Methadone is now associated with more deaths than any other prescription painkiller, according to the CDC. There is a therefore a need for a treatment that rids the patient of drug dependency including opioid and methadone dependency.

Noribogaine, also known as 12-hydroxyibogaine or 12-O-demethylibogaine, is a dominant metabolite of ibogaine. Noribogaine can be depicted by the following formula:

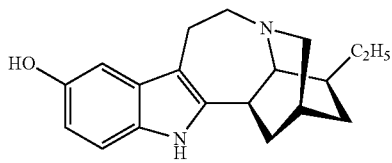

Noribogaine and its pharmaceutically acceptable salts have recently received significant attention as a non-addictive alkaloid for the treatment of drug dependency (U.S. Pat. No. 6,348,456).

SUMMARY OF THE INVENTION

This invention is based on the discovery that noribogaine negatively interacts with methadone, such administration of noribogaine to mammal concurrently being administered methadone at high doses surprisingly exacerbates methadone's negative side-effects, including the risk of death. Based on this discovered interaction between methadone and noribogaine, it is important that (a) methadone is not administered during or shortly after noribogaine administration; (b) methadone therapy is discontinued prior to noribogaine administration and/or (c) patients are screened for methadone levels prior to administration of noribogaine. The interaction between methadone and noribogaine is relevant to several different classes of patients.

In one aspect of the invention, the patient is on methadone therapy. As the amount of methadone in the plasma of a methadone treated patient is dependent on that patient's methadone intake, rate of metabolism and other factors, the direct administration of noribogaine to a methadone treated patient is contra-indicated. Therefore, based on this discovered interaction between methadone and noribogaine, prior to initiation of noribogaine treatment, a patient on methadone therapy undergoes a period of methadone abstinence to wash out all or substantially all of the methadone.

Accordingly, in a related aspect of the invention, there is provided a method for pretreating an opioid addicted patient undergoing methadone therapy such that the patient qualifies for noribogaine therapy to treat the underlying opioid addiction which method comprises maintaining the patient on a methadone abstinence regimen until sufficient methadone has been removed from the patient's serum thereby allowing said patient to undergo noribogaine therapy.

In another related aspect of the invention, there is provided a method for treating addiction in an opioid addicted patient undergoing methadone therapy which method comprises confirming that a sufficient amount of methadone has been removed from the patient's serum and then administering a therapeutic amount of noribogaine, a noribogaine derivative or a pharmaceutically acceptable salt thereof to said patient under conditions wherein the patient is no longer opioid addicted.

In still another aspect, the invention includes a method for addiction cessation in a human patient whose addiction is treated with methadone, the method comprising: (a) initiating and maintaining methadone abstinence in the patient for a period of time sufficient to remove all or substantially all of the methadone from the patient's serum; and (b) administration of noribogaine, a noribogaine derivative or a pharmaceutically acceptable salt thereof to said patient under conditions wherein the patient is no longer addicted. The level of methadone or methadone metabolites may be monitored in the mammal, such in a body fluid. The period of time sufficient to remove methadone from the body (i.e. until the level of methadone is reduced to an acceptable risk tolerance level) may be adjusted according to the mammal, their physiologic state, metabolic rate, and the like. In one embodiment, the time sufficient to remove methadone from the body is a period of at least one day, typically several days, a week, or more. In another embodiment, the amount of methadone removed from the body is evaluated by blood tests and preferably all or substantially all of the methadone is removed prior to initiation of noribogaine therapy.

Surprisingly, noribogaine can be administered relatively safely to a patient who has been administered (or to whom will be administered) morphine. The basis of this greater safety of noribogaine with morphine is unknown. Morphine and other opioids having short serum half-lives in the patient are removed from the patient after administration is terminated, so that noribogaine can be administered. Therefore, the methadone regimen may be replaced with morphine or such other opioids prior to noribogaine treatment. However, as morphine satisfies the patient's addiction while exhibiting acceptable short term side effects, cessation of methadone is preferably conducted with the concurrent administration of morphine as the short serum half-life opioid. An extended release morphine may be administered, for example. In a further aspect, the cessation of methadone administration occurs through a gradual reduction in the dose or frequency of administration of methadone. The gradual reduction in the dose or frequency of administration of methadone may be matched with gradual increase in the dose or frequency of administration of a non-methadone opioid.

In addition to those patients in methadone clinics, the risk of negative interactions between noribogaine and methadone is especially acute in the population of drug users (i.e., not in methadone clinics), who may fail to report prior administration of methadone or may have unwittingly taken methadone as a contaminant in other drugs. Accordingly, in another aspect of the invention, the patient is not on methadone therapy. In this aspect, the patient may or may not be addicted to opioids. Such a patient may have been administered methadone either as prescribed for the treatment of pain, or as a behavior associated with addiction. For example, drug addicts may take a variety of drugs and drug cocktails, of indeterminate quality and purity. Accordingly, a patient may have been administered methadone without being on methadone therapy.

Therefore, in the treatment of addiction in a human patient, the clinician must evaluate the methadone exposure and/or the presence of methadone in the body so as to assess whether and when to initiate noribogaine therapy. Methadone exposure may be assessed through questionnaires and/or assays for the presence of methadone or methadone metabolites in a body fluid. The prevention of methadone exposure may also be facilitated by placing the patient in hospital or other controlled environment.

The negative drug interactions between noribogaine and methadone may also occur with other drugs. In some embodiments, the exposure to, and presence of, such other drugs is determined prior to administration of noribogaine.

In another aspect, the patient has been administered noribogaine, and the invention concerns the treatment of the patient after administration of noribogaine. Negative drug interactions may also occur in patients who have been administered noribogaine, and are subsequently administered methadone or another drug that adversely interacts with noribogaine. Accordingly, in one embodiment, the patient is maintained in a clinical/controlled setting until the patient is addiction free and the presence of noribogaine in the patient is removed or substantially removed. Alternatively, the patient may be administered morphine in place of other drugs. However, it is important to note that while the initial treatment of noribogaine can treat physiological addiction, behavioral addiction may cause relapse in the treated patient.

In further aspects, the patient may require multiple rounds of administration of noribogaine. In this aspect, a method of reducing the likelihood and severity of negative interactions between noribogaine and a second drug includes the determining the level of such second drug, or its metabolite, and/or controlling access to the second other drug. When the other drug is methadone, the method includes determining the level of methadone or a methadone metabolite in the patient prior to administration of noribogaine. In one embodiment, the level of methadone or a methadone metabolite is determined through examination of a sample from the patient. In another embodiment, the patient is administered a series of questions to determine the likelihood of methadone administration. In another embodiment, the patient is placed in a controlled environment to prevent access to methadone.

In further aspects, the invention includes kits and compositions for the treatment of addiction, and which contain suitable reagents for the treatment of addiction, detecting the presence of methadone and/or noribogaine.

The invention also includes methods of counselling a patient of the risk of negative interactions between methadone and noribogaine. In related embodiments, the invention includes materials to educate counselors and patients.

While noribogaine has been disclosed for treatment of substance addiction, its use in humans is complicated by the fact that the ranges in the prior art are exceptionally broad (0.01 to 1000 mg/kg body weight). Furthermore, human clinical studies demonstrate that the lower dosing of noribogaine has minimal impact on withdrawal symptoms in addicted patients. Thus, the previously disclosed broad range has now been found to be insufficient for human therapy at the lower end of this range.

Moreover, the use of noribogaine imparts a dose dependent prolongation of the treated patient's QT interval, rendering higher dosing of noribogaine unacceptable. A prolonged QT interval is a marker of potential Torsades de Pointes, a serious arrhythmia that can result in death.

Treatment with a narrow dosage range of noribogaine, noribogaine derivative, or pharmaceutically acceptable salt or solvate thereof provides a therapeutic reduction in withdrawal symptoms and/or an increase in time to resumption of opioid use in addicted patients. In some embodiments, the patient is administered a unit dose of noribogaine or noribogaine derivative that provides an average serum concentration of 50 ng/mL to 180 ng/mL, said concentration being sufficient to inhibit or ameliorate said addiction while maintaining a QT interval of less than about 500 ms during said treatment. In some embodiments, the unit dose provides an acceptable QT interval prolongation of less than 50 milliseconds. In some embodiments, the unit dose provides an acceptable QT interval prolongation of less than 30 milliseconds. In some embodiments, the unit dose provides an acceptable QT interval prolongation of less than 20 milliseconds.

In some embodiments, the patient is administered an initial dose of noribogaine, noribogaine derivative, or pharmaceutically acceptable salt or solvate thereof, followed by one or more additional doses. In one embodiment, the initial dose is from 50 mg to 120 mg. In one embodiment, the one or more additional doses are lower than the initial dose. In one embodiment, the one or more additional doses are from 5 mg to 75 mg. In one embodiment, such a dosing regimen provides an average serum concentration of noribogaine of 50 ng/mL to 180 ng/mL. In one embodiment, the one or more additional doses maintain an average serum concentration of 50 ng/mL to 180 ng/mL over a period of time. In one embodiment, the one or more additional doses are administered periodically.

BRIEF DESCRIPTION OF THE DRAWINGS

FIG. 1A is normally scaled.

DETAILED DESCRIPTION

Figure 1A:
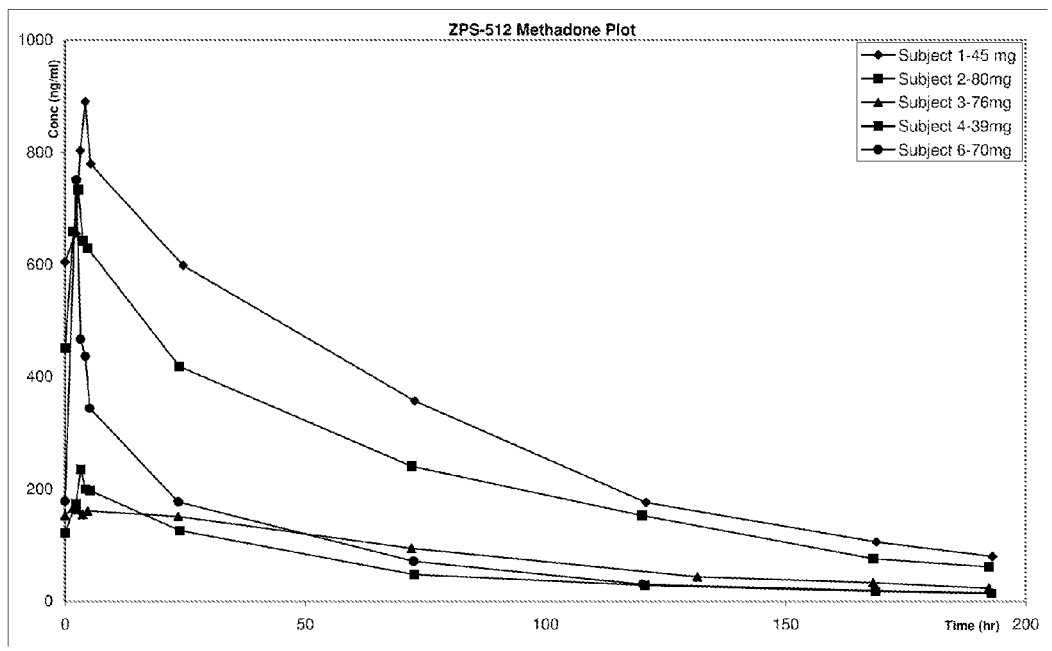
FIG. 1A shows the serum concentration (ng/ml) of methadone in healthy patients after administration of a single dose of methadone, in amounts ranging from 39 to 80 mg.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. Thus, for example, reference to "a compound" includes a plurality of compounds.

1. Definitions

Unless defined otherwise, all technical and scientific terms used herein have the same meaning as commonly understood by one of ordinary skill in the art to which this invention belongs. As used herein the following terms have the following meanings.

The term "about" when used before a numerical designation, e.g., temperature, time, amount, and concentration, including a range, indicates approximations which may vary by (+) or (−) 20%, 10%, 5% or 1%. Preferably, the term "about" when used with regard to a dose amount means that the dose may vary by +/−20%. For example, "about 2 mg/kg noribogaine" indicates that a patient may be administered a dose of noribogaine between 1.6 mg/kg and 2.4 mg/kg. In another example, about 120 mg per unit dose of noribogaine indicates that the unit dose may range from 96 mg to 144 mg.

The term "mammal" refers to any mammalian species including without limitation mice, rats, rabbits, dogs, primates and, in particular, humans.

"Addictive" refers to a compound that, when administered to a mammal can create a dependence of the mammal on the compound. A therapeutic effect amount of an addictive compound on a mammal may decrease with prolonged administration of the addictive compound. When administered to a mammal, an addictive compound may also create a craving in the mammal for more of it. Morphine, heroine, methadone, fentanyl, and the like are addictive compounds: specifically, addictive opioids. Other "addictive drugs" include, without limitation:

(A) Stimulants (psychological addiction, moderate to severe; withdrawal is purely psychological and psychosomatic): Amphetamine, methamphetamine, Cocaine, Caffeine, Nicotine (B) Sedatives and hypnotics (psychical addiction, mild to severe, and physiological addiction, severe; abrupt withdrawal may be fatal): Alcohol, Barbiturates, glutethimide; Benzodiazepines, particularly alprazolam, flunitrazepam, triazolam, temazepam, and nimetazepam; Z-drugs like zopiclone (which have a similar effect in the body to benzodiazepines); Methaqualone and the related quinazolinone sedative-hypnotics (C) Opiate and opioid analgesics (psychical addiction, mild to severe, physiological addiction, mild to severe; abrupt withdrawal is unlikely to be fatal): Morphine and codeine, the two naturally occurring opiate analgesics; Semi-synthetic opiates, such as heroin (diacetylmorphine; morphine diacetate), oxycodone, buprenorphine, and hydromorphone; fully synthetic opioids, such as fentanyl, meperidine/pethidine, and methadone.

In preferred embodiments, the addictive drugs to be treated are opiates, opioids, cocaine, and/or alcohol. In contrast, noribogaine is not an addictive compound or "addictive drug."

Likewise, "treating addiction" in a mammal refers to a course of action that decrease the physiological dependence or craving for the addictive substance. The addiction can be to methadone, other opioids, or any other addictive compound.

"Treating addiction in a mammal being administered methadone" refers to the fact that the mammal is, or is suspected of being, administered methadone. This relates to the risk of a negative interaction between methadone and noribogaine. It is not to be taken as limiting the scope of mammals to those who are addicted to methadone, or other opioids. For example, a mammal may be addicted to nicotine, alcohol or another compound, and is administered methadone for treatment of the addiction. It may also be that methadone is administered to the mammal for provision of analgesia (treatment of pain).

"Administration" refers to introducing an agent into a patient. Typically, an effective amount is administered, which amount can be determined by the treating physician or the like. Any route of administration, such as oral, topical, subcutaneous, peritoneal, intraarterial, inhalation, vaginal, rectal, nasal, introduction into the cerebrospinal fluid, or instillation into body compartments can be used. In a preferred embodiment, administration is oral. The related terms and phrases "administering" and "administration of", when used in connection with a compound or pharmaceutical composition (and grammatical equivalents) refer both to direct administration, which may be administration to a patient by a medical professional or by self-administration by the patient, and/or to indirect administration, which may be the act of prescribing a drug. For example, a physician who instructs a patient to self-administer a drug and/or provides a patient with a prescription for a drug is administering the drug to the patient.

For administration of noribogaine or derivative thereof, the amount may be between 5 mg and 120 mg. In some embodiments, the dose of noribogaine or derivative thereof is 5, 10, 20, 25, 30, 40, 50, 60, 70, 75, 80, 90, 100, 110, or 120 mg. Preferably, the unit dose is between 20 mg and 120 mg per patient per day.

Alternatively, the administration of noribogaine may be determined by serum $C_{max}$ and or AUC, in order to obtain a therapeutic dose. Administration of a single dose of 30 mg noribogaine free base under fasting conditions gives a $C_{max}$ of 55.9 ng/ml at 1.75 hours after administration, with a mean AUC/24 h of 29.2 ng/ml.

For a single dose of 60 mg noribogaine free base under fasting conditions, the mean $C_{max}$ of 116 ng/ml was observed between 1.75 hours after administration, while the mean AUC/24 h of 61 ng/ml was obtained.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "substantial" is used to refer to an amount that produces a significant effect. Therefore "without providing any substantial amount" doesn't exclude a small amount that produces little or no effect in the patient. Similarly, the term "substantial proportion" refers to more than about 50% in some cases. It could also refer to more than about 60%, more than about 70%, more than about 80%, more than about 90%, more than about 95%, or more than about 99%.

The term "substantially all" as used herein refers to a level of drug, such as methadone or noribogaine that is below a level associated with a significant risk of negative interaction. If the level of the drug removed is substantially all of the drug in the mammal, that animal is "negative" for the presence of that certain drug. If the level of the drug removed is not substantially all of that drug in the mammal, that animal is "positive" for the presence of the drug.

"The level associated with a significant risk of negative interaction" will vary according to the patient and, especially, the tolerance for the drug. During addiction, the patient will typically have increased the dose and/or frequency of administration such that the level of drug tolerated by the patient would be seriously harmful, and even fatal, to a patient who has not been previously administered the drug. After treatment for addiction, and a period of abstinence, the level of tolerance typically declines. Accordingly, tolerance may be determined by a physician or other qualified person.

A level not associated with a significant risk of negative interaction may be safely assumed as $1/10^{th}$ of the IC50 of the drug. In other embodiments, a level not associated with a significant risk of negative interaction may be more than 10% of the $IC_{50}$, such as 20%, 25%, 30%, 40% and 50% of the IC50.

For noribogaine, the lowest IC50 is 0.04 µM, A serum level of 0.004 uM (4 nM) or below is not associated with a significant risk of negative interaction and qualifies as "substantially all" of the drug being absent.

For methadone, the therapeutic level of methadone ranges from 0.03-0.56 mg/L, according to the US National highway traffic safety administration (www.nhtsa.gov/people/injury/research/job185drugs/methadone.htm). Accordingly, a patient from whose serum substantially all methadone has been removed has a serum level of methadone ranging from 1 to 50% of the initial methadone levels in the blood and, in one preferred embodiment, from 3 µg/L to 56 µg/L.

Figure 1B:
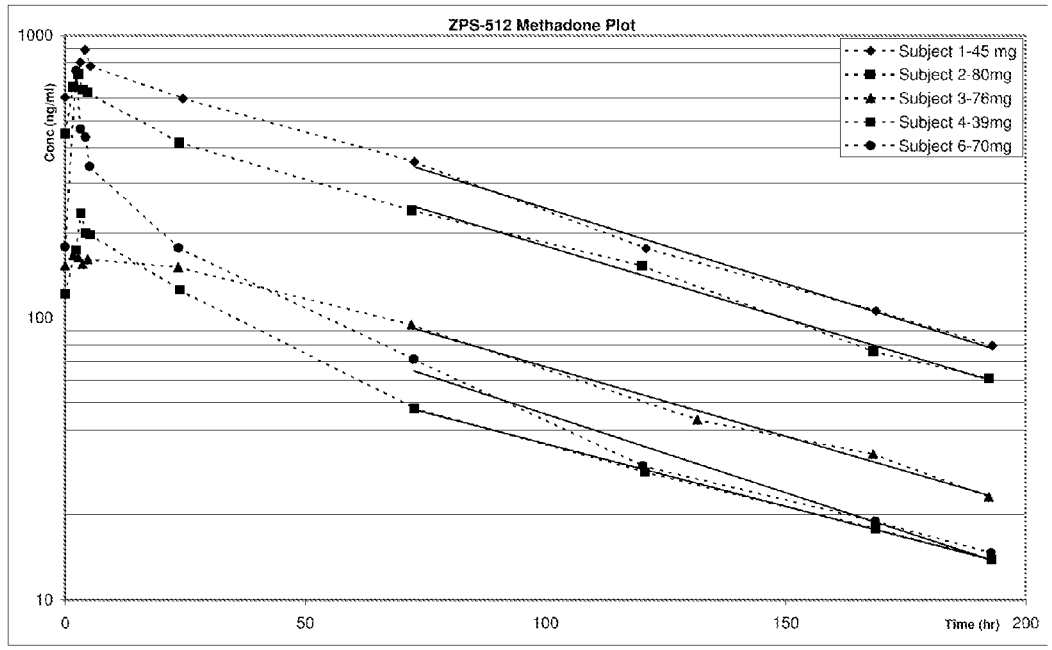
FIG. 1B shows the serum concentration (ng/ml) of methadone in healthy patients after administration of a single dose of methadone, in amounts ranging from 39 to 80 mg, on a logarithmic scale.

FIGS. 1A-B show the serum concentration (ng/ml) of methadone in healthy patients after administration of a single dose of methadone. After 200 hours, the serum level of methadone is typically 10% of the Cmax.

The level of methadone may be determined directly or from metabolites. The primary inactive metabolites of methadone are 2-ethylidene-1,5-dimethyl-3,3diphenylpyrrolidine (EDDP) and 2-ethyl-5-methyl-3,3-diphenyl-1-pyrroline (EMDP), and may be measured in, e.g., serum and urine. The percentage of a dose excreted in the urine as unchanged methadone and EDDP will vary with the pH of the urine. Urinary excretion of unchanged parent drug is 5-50% and EDDP 3-25%.

"Mu (or µ) opioid receptor" or "mu (or µ) receptor" refers to a class of opioid receptors with higher affinity for enkephalins and beta-endorphins but with lower affinity for dynorphins Mu receptors can mediate acute changes in neuronal excitability via dis-inhibition of presynaptic release of GABA. Mu receptor agonists are compounds that activate the mu receptor and mu receptor antagonists are compounds that prevent activation of the mu receptor.

The term "higher-affinity mu receptor agonist" refers to a compound having an affinity constant (K value) lower than another compound. For example, noribogaine has been reported to have an affinity constant (K value) of 2.66 for the mu receptor and ibogaine has been reported to have an affinity constant (K value) of 11.04 for the mu receptor (Pearl et al., Brain Research, 675:342-344 (1995)). As such, noribogaine is a higher-affinity mu receptor agonist than ibogaine.

"Noribogaine" refers to the compound:

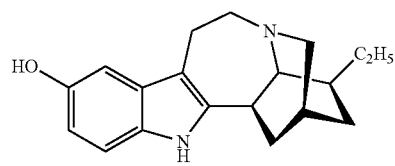

or its pharmaceutically acceptable salt, or solvates of each thereof. Noribogaine binds to the mu receptor that is associated with pain relief and euphoria. It should be understood that where "noribogaine" is mentioned herein, one more polymorphs of noribogaine can be utilized and are contemplated. In some embodiments, noribogaine is noribogaine glucuronide. Noribogaine is prepared by demethylation of naturally occurring ibogaine:

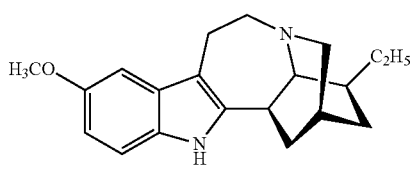

which is isolated from *Tabernanth iboga*, a shrub of West Africa. Demethylation may be accomplished by conventional techniques such as by reaction with boron tribromide/methylene chloride at room temperature followed by conventional purification. See, for example, Huffman, et al., J. Org. Chem. 50:1460 (1985). Noribogaine can be synthesized as described, for example in U.S. Patent Pub. Nos. 2013/0165647, 2013/0303756, and 2012/0253037, PCT Patent Publication No. WO 2013/040471 (includes description of making noribogaine polymorphs), and U.S. patent application Ser. No. 13/593,454, each of which is incorporated herein by reference in its entirety.

"Noribogaine derivatives" refer to those derivatives of noribogaine found in U.S. Pat. Nos. 6,348,456 and 8,362,007; as well as in U.S. patent application Ser. No. 13/165,626; and US Patent Application Publication Nos. US2013/0131046; US2013/0165647; US2013/0165425; and US2013/0165414. Each of the above patents and patent applications are incorporated by reference in its entirety.

Preferably, the present invention provides preferred derivatives of noribogaine such as those having the formula:

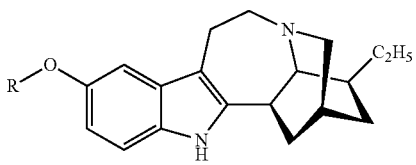

wherein R is hydrogen or a hydrolyzable group, such as hydrolysable esters of from about 1 to 12 carbons or a sulfate or phosphate group. Such compounds may be administered either as single compounds, mixtures of compounds or as composition. Generally, in the above formula, R is a hydrogen or a group of the formula:

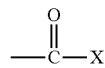

wherein X is a $C_1$-$C_{12}$ group, which is unsubstituted or substituted. For example, X may be a linear alkyl group such as methyl, ethyl, n-propyl, n-butyl, n-pentyl, n-hexyl, n-heptyl, n-octyl, n-nonyl, n-decyl, n-undecyl or n-dodecyl, or a branched alkyl group, such as i-propyl or sec-butyl. Also, X may be a phenyl group or benzyl group, either of which may be substituted with lower alkyl groups or lower alkoxy groups. Generally, the lower alkyl and/or alkoxy groups have from 1 to about 6 carbons. For example, the group R may be acetyl, propionyl or benzoyl. However, these groups are only exemplary. Generally, for all groups X, they may either be unsubstituted or substituted with lower alkyl or lower alkoxy groups. For example, substituted X may be o-, m- or p-methyl or methoxy benzyl groups.

Also encompassed within this invention are derivatives of noribogaine that act as prodrug forms of noribogaine. A prodrug is a pharmacological substance administered in an inactive (or significantly less active) form. Once administered, the prodrug is metabolized in vivo into an active metabolite. In the context of the present claims, "noribogaine derivative" does not include ibogaine.

The present invention is not limited to any particular chemical form of noribogaine and the drug may be given to patients either as a free base or as a pharmaceutically acceptable acid addition salt. In the latter case, the hydrochloride salt is generally preferred, but other salts derived from organic or inorganic acids may also be used. Examples of such acids include, without limitation, hydrobromic acid, phosphoric acid, sulfuric acid, methane sulfonic acid, phosphorous acid, nitric acid, perchloric acid, acetic acid, tartaric acid, lactic acid, succinic acid, citric acid, malic acid, maleic acid, aconitic acid, salicylic acid, thalic acid, embonic acid, enanthic acid, and the like. As discussed above, noribogaine itself may be formed from the O-demethylation of ibogaine which, in turn, may be synthesized by methods known in the art (see e.g., Huffman, et al., J. Org. Chem. 50:1460 (1985)).

"Opiate" refers to a compound extracted from poppy pods and their semi-synthetic counterparts which bind to the opioid receptors.

"Opioid" refers to a compound that binds to the opioid receptors, including but not limited to mu receptors. Opioids include the opiates and any synthesized drug that attaches itself to the opioid receptors.

A "synthetic opioid" is a synthetic narcortic that has properties of naturally occurring opiates such as binding to the opioid receptors. Examples of synthetic opioids include methadone, fentanyl, alphamethylfentanyl, alfentanil, sulfentanil, remifentanil, carentanyl, ohmefentanyl, pethidine, ketobemidone, MPPP, allyprodine, prodine, pepap, propoxyphene, dextropropoxphene, dextromoramide, bezitramide, piritramide, methadone, dipipanone, levomethadyl acetate, difenoxin, diphenolylate, loperamide, dezocine, pentazocine, phenazocine, buprenophine, dihydroetorphine, etorphine, butorphanol, nalbuphine, levorphanol, levomethorphan, lefetamine, meptazinol, tilidine, tramadol, tapentadol, nalmefene, naloxone, and naltrexone.

"Methadone" is an addictive synthetic opioid, used medically as an analgesic, an antitussive and a maintenance anti-addictive for use in patients dependent on opioids. The term "methadone" also refers to derivatives of methadone.

"Morphine" is a potent opiate medication. It is the most abundant alkaloid found in opium. It is a powerful analgesic used to relieve severe or agonizing pain. Although morphine has a high potential for addiction, physical addiction may take several months to develop.

"Pharmaceutically acceptable composition" refers to a composition that is suitable for administration to a mammal, particularly, a human. Such compositions include various excipients, diluents, carriers, and such other inactive agents well known to the skilled artisan.

"Pharmaceutically acceptable salt" refers to pharmaceutically acceptable salts, including pharmaceutically acceptable partial salts, of a compound, which salts are derived from a variety of organic and inorganic counter ions well known in the art and include, by way of example only, hydrochloride, hydrobromide, tartrate, mesylate, acetate, maleate, oxalate and the like, and when the molecule contains an acidic functionality, include, by way of example only, sodium, potassium, calcium, magnesium, ammonium, tetraalkylammonium, and the like.

A "drug exhibiting a negative interaction with noribogaine" can be determined by animal studies and/or clinical trials. The mechanism of the negative interaction between methadone and noribogaine is unknown. Three classes of drugs are of particular concern for possible negative interaction with noribogaine. The first class are mu agonists, such as methadone. The second class are drugs that cause respiratory depression. Drugs that cause respiratory depression include alcohol, benzodiazepines, barbiturates, GHB, and sedatives. Strong opiates (fentanyl, heroin, morphine, etc.), barbiturates, and the benzodiazepine, temazepam, are particularly notorious for respiratory depression.

The third class of drugs are those that prolong the QT interval, i.e. the period of time between the Q and T wave in the heart's electrical cycle. Excessive QT elongation is a risk factor for arrhythmia and sudden death. Methadone is well known for prolonging the QT interval of the heart. Other drugs also known for causing QT elongation include clarithromycin (Biaxin®), levofloxacin, haloperidol (Haldol®), especially when taken concomitantly with a specific cytochrome P450 inhibitor like fluoxetine (Prozac®), cimetidine (Tagamet®) or grapefruit. Other examples include amiodarone, lithium, chloroquine, erythromycin, phenothiazines, sotalol, procainamide, quinidine, and cisapride (Propulsid®).

Elongation of the QT interval may also occur with diarrhea, hypomagnesemia and hypokalemia. Hypomagnesemia and hypokalemia is often observed in malnourished individuals and chronic alcoholics. Accordingly, in some embodiments, the general health of the patient is assessed prior to administration of noribogaine, with special attention to serum levels of salts and hydration, particularly Magnesium and Potassium. In one embodiment, dehydration, hypomagnesemia and/or hypokalemia are treated prior to administration of noribogaine.

The risk of excessive QT elongation is most pronounced in those with pre-existing QT elongation. Accordingly, in some embodiments, prior to the administration of noribogaine, the patient is examined for QT elongation and arrythmias. According to the best clinical judgment, some patients are contraindictated for noribogaine administration.

"Therapeutically effective amount" refers to an amount of a drug or an agent that, when administered to a patient suffering from a condition, will have the intended therapeutic effect, e.g., alleviation, amelioration, palliation or elimination of one or more manifestations of the condition in the patient. The therapeutically effective amount will vary depending upon the subject and the condition being treated, the weight and age of the subject, the severity of the condition, the salt, solvate, or derivative of the active drug portion chosen, the particular composition or excipient chosen, the dosing regimen to be followed, timing of administration, the manner of administration and the like, all of which can be determined readily by one of ordinary skill in the art. The full therapeutic effect does not necessarily occur by administration of one dose, and may occur only after administration of a series of doses. Thus, a therapeutically effective amount may be administered in one or more administrations. For example, and without limitation, a therapeutically effective amount of an agent, in the context of treating drug dependency, refers to an amount of the agent that attenuates the dependency and/or statistically presents little or no risk of relapse to illicit drug use.

A "therapeutic level" of noribogaine is an amount of noribogaine that is sufficient to attenuate a drug dependency but not high enough to pose any significant risk to the patient. Therapeutic levels of drugs can be determined by tests that measure the actual concentration of the compound in the blood of the patient. This concentration is referred to as the "serum concentration." It is understood that the therapeutic level will depend upon the weight, age, condition and degree of addiction of the patient and that such factors are readily ascertainable by the skilled clinician based on the teachings herein.

The term "dose" refers to a range of noribogaine, noribogaine derivative, or pharmaceutical salt or solvate thereof that provides a therapeutic serum level of noribogaine when given to a patient in need thereof. The dose is recited in a range, for example from 20 mg to 120 mg, and can be expressed either as milligrams or as mg/kg body weight. The attending clinician will select an appropriate dose from the range based on the patient's weight, age, degree of addiction, health, and other relevant factors, all of which are well within the skill of the art.

The term "unit dose" refers to a dose of drug that is given to the patient to provide therapeutic results, independent of the weight of the patient. In such an instance, the unit dose is sold in a standard form (e.g., 20 mg tablet). The unit dose may be administered as a single dose or a series of subdoses. In some embodiments, the unit dose provides a standardized level of drug to the patient, independent of weight of patient. Many medications are sold based on a dose that is therapeutic to all patients based on a therapeutic window. In such cases, it is not necessary to titrate the dosage amount based on the weight of the patient.

The term "attenuating," "attenuated," or "attenuation" as it applies to drug dependency refers to stabilizing patients and preventing and/or alleviating withdrawal symptoms.

"The amount of addictive synthetic opioid maintained in the patient" refers to the serum concentration of the addictive synthetic opioid in the patient either once tapering of that opioid is initiated or after cessation of administration of that opioid. "The amount of the noribogaine or the noribogaine derivative administered to or maintained in the patient" refers to a serum concentration of noribogaine or the noribogaine derivative in the patient that is at least as much as the serum concentration that is effective for therapy. The serum concentration of an administered agent may reduce, for example, due to metabolism and/or excretion.

The term "under the influence" refers to having a measurable serum concentration of an agent.

"Sub-therapeutic" refers to amounts of noribogaine which when administered either in a single or multiple doses achieve therapeutic serum concentration. A sub-therapeutic serum concentration of noribogaine is typically less than 30 ng/ml, more preferably less than 10 ng/ml.

"Tapering" refers to the reduction in the amount of, e.g., addictive synthetic opioid agent administered to the patient such that the amount becomes sub-therapeutic and preferably is no longer administered. Tapering occurs over a period of time either in a step wise fashion (e.g., a full dose for 1 hour, 80% of the full dose for 1 hour, 60% of the full dose for 1 hour, etc.) or in a continuous manner (e.g., a intravenous drip wherein the amount of the alkaloid analgesic agent is continuously reduced by, for example, computer assisted controls).

"Treatment", "treating", and "treat" are defined as acting upon a disease, disorder, or condition with an agent to reduce or ameliorate harmful or any other undesired effects of the disease, disorder, or condition and/or its symptoms. "Treatment," as used herein, covers the treatment of a human patient, and includes: (a) reducing the risk of occurrence of the condition in a patient determined to be predisposed to the disease but not yet diagnosed as having the condition, (b) impeding the development of the condition, and/or (c) relieving the condition, i.e., causing regression of the condition and/or relieving one or more symptoms of the condition.

"Treating" or "treatment of" a condition or patient refers to taking steps to obtain beneficial or desired results, including clinical results such as the reduction of symptoms. For purposes of this invention, beneficial or desired clinical results include, but are not limited to, attenuation of dependency, reduced or no dependence on an addictive opioid analgesic agent, and the like.

"Treating addiction" is defined as a reduction in addictive behavior. This may be determined by a reduction in craving or dependency, such as may be measured in psychological assays or behavioral changes. A behavioral change in addiction may be measured by a reduction in the amount and/or frequency of use of the addictive substance. A period of complete abstinence of use of the addictive drug for at least two weeks is strong evidence of treatment. Treatment may also be determined by measuring the level of drugs and metabolites in the patient.

"Treating addiction" or "treatment of addiction" may also be considered to have at least two separate phases.

The first phase is treatment of withdrawal from the drug of addiction, herein known as "withdrawal" or "withdrawing". This is often referred to as acute withdrawal. Withdrawal from drug dependence is characterized by dramatic and traumatic symptoms, including sweating, racing heart, palpitations, muscle tension, tightness in the chest, difficulty breathing, tremor, nausea, vomiting, diarrhea, grand mal seizures, heart attacks, strokes, hallucinations and delirium tremens (DTs). Numerous treatments have been developed in attempts to ameliorate such symptoms. For example, a reduction in the dose of the addictive drug, and/or its replacement with a less addictive or less harmful drug ameliorating the symptoms of withdrawal. Administration of noribogaine is effective in reducing in ameliorating the symptoms of withdrawal.

The second phase is treatment of the behavioral aspects of addiction, also referred to as long-term or post-acute withdrawal. Addictive behavior is typically initiated and maintained because, in part, the patient enjoys the experience of drug administration. In addition, long-term changes in the brain may occur due to addiction, and these can increase the likelihood of relapse. Accordingly, relapse is common. In this phase, success may be measured by a combination of factors, such as (i) reduction in craving (ii) increase in the period of abstinence (iii) reduction of "binge" behavior (iv) reduction in the dose of drug taken (v) reduction in harmful behavior. Repeated treatments may be required. Administration of noribogaine is effective in reducing the behavioral aspects of addiction, although repeat treatments may be required. Such repeat treatments may be (a) as-needed intermittent basis or (b) continuous.

In some embodiments, a discrete administration of noribogaine is effective. That is, noribogaine is administered in one or a few doses over a period of hours. In some embodiments, administration is terminated, until all or substantially all of the noribogaine has been removed from the serum. The dissociative properties of noribogaine are particularly useful in this model of therapy.

In an alternative embodiment, noribogaine is administered repeatedly to maintain a certain level of noribogaine in the serum. Noribogaine is nonaddictive, and is therefore preferable to other "replacement therapy" drugs, such as methadone.

In the context of long term administration of noribogaine to a patient, the invention includes methods of preventing the administration to the patient of to drugs that negatively interact with noribogaine, such as methadone.

As used herein, the term "patient" refers to mammals and includes humans and non-human mammals.

METHODS OF THE INVENTION

In one embodiment, the invention relates to a method for treating addiction in a patient being administered methadone, the method comprising: (a) replacing methadone administration with a noribogaine-compatible opioid (e.g., morphine) or derivative thereof for a period of time until the serum level of methadone is reduced to a level that is safe to administer noribogaine; and (b) administering a unit dose of noribogaine or a noribogaine derivative to the patient, wherein the unit dose provides an average serum concentration of 50 ng/mL to 180 ng/mL, said concentration being sufficient to inhibit or ameliorate said addiction while maintaining a QT interval of less than about 500 ms during said treatment. In some embodiments, the concentration is sufficient to attenuate said symptoms while maintaining a QT interval of less than about 470 ms during treatment. Preferably, the concentration is sufficient to attenuate said symptoms while maintaining a QT interval of less than about 450 ms during treatment. In one embodiment, the concentration is sufficient to attenuate said symptoms while maintaining a QT interval of less than about 420 ms during treatment. In one embodiment, the withdrawal symptoms are symptoms of acute withdrawal.

In one aspect, the patient is administered a dosage of noribogaine, noribogaine derivative, or pharmaceutically acceptable salt or solvate thereof that provides an average serum concentration of 80 ng/mL to 100 ng/mL, said concentration being sufficient to attenuate said symptoms while maintaining a QT interval of less than about 500 ms during said treatment. In some embodiments, the concentration is sufficient to attenuate said symptoms while maintaining a QT interval of less than about 470 ms during treatment. Preferably, the concentration is sufficient to attenuate said symptoms while maintaining a QT interval of less than about 450 ms during treatment. In one embodiment, the concentration is sufficient to attenuate said symptoms while maintaining a QT interval of less than about 420 ms during treatment. In one embodiment, the withdrawal symptoms are symptoms of acute withdrawal.

In one embodiment, the QT interval is not prolonged more than about 50 ms. In one embodiment, the QT interval is not prolonged more than about 40 ms. In one embodiment, the QT interval is not prolonged more than about 30 ms. In one embodiment, the QT interval is not prolonged more than about 20 ms. In one embodiment, prolongation of the QT interval is equivalent to or less than the prolongation observed for methadone-treated patients.

In one embodiment, the average serum concentration of noribogaine is from 50 ng/mL to 180 ng/mL, or 60 ng/mL to 180 ng/mL. In one embodiment, the average serum concentration of noribogaine is from 50 ng/mL to 150 ng/mL, or 60 ng/mL to 150 ng/mL. In one embodiment, the average serum concentration of noribogaine is from 50 ng/mL to 100 ng/mL, or 60 ng/mL to 100 ng/mL. In one embodiment, the average serum concentration of noribogaine is from 80 ng/mL to 150 ng/mL. In one embodiment, the average serum concentration of noribogaine is from 80 ng/mL to 100 ng/mL. The ranges include both extremes as well as any subranges between.

In one embodiment, the dosage or aggregate dosage of noribogaine, noribogaine derivative, or salt or solvate thereof is from 1 mg/kg to 4 mg/kg body weight per day. The aggregate dosage is the combined dosage, for example the total amount of noribogaine, noribogaine derivative, or pharmaceutically acceptable salt or solvate thereof administered over a 24-hour period where smaller amounts are administered more than once per day. In one embodiment, the dosage or aggregate dosage of noribogaine, noribogaine derivative, or salt or solvate thereof is from 1.3 mg/kg to 4 mg/kg body weight. In one embodiment, the dosage or aggregate dosage of noribogaine, noribogaine derivative, or salt or solvate thereof is from 1.3 mg/kg to 3 mg/kg body weight. In one embodiment, the dosage or aggregate dosage of noribogaine, noribogaine derivative, or salt or solvate thereof is from 1.3 mg/kg to 2 mg/kg body weight. In one embodiment, the dosage or aggregate dosage of noribogaine, noribogaine derivative, or salt or solvate thereof is from 1.5 mg/kg to 3 mg/kg body weight. In one embodiment, the dosage or aggregate dosage of noribogaine, noribogaine derivative, or salt or solvate thereof is from 1.7 mg/kg to 3 mg/kg body weight. In one embodiment, the dosage or aggregate dosage of noribogaine, noribogaine derivative, or salt or solvate thereof is from 2 mg/kg to 4 mg/kg body weight. In one embodiment, the dosage or aggregate dosage of noribogaine, noribogaine derivative, or salt or solvate thereof is from 2 mg/kg to 3 mg/kg body weight. In one embodiment, the dosage or aggregate dosage of noribogaine, noribogaine derivative, or salt or solvate thereof is about 2 mg/kg body weight. The ranges include both extremes as well as any subranges there between.

In one embodiment, the dosage or aggregate dosage of noribogaine, noribogaine derivative, or salt or solvate thereof is about 4 mg/kg body weight per day. In one embodiment, the dosage or aggregate dosage of noribogaine, noribogaine derivative, or salt or solvate thereof is about 3 mg/kg body weight per day. In one embodiment, the dosage or aggregate dosage of noribogaine, noribogaine derivative, or salt or solvate thereof is about 2 mg/kg body weight per day. In one embodiment, the dosage or aggregate dosage of noribogaine, noribogaine derivative, or salt or solvate thereof is about 1.7 mg/kg body weight per day. In one embodiment, the dosage or aggregate dosage of noribogaine, noribogaine derivative, or salt or solvate thereof is about 1.5 mg/kg body weight per day. In one embodiment, the dosage or aggregate dosage of noribogaine, noribogaine derivative, or salt or solvate thereof is about 1.3 mg/kg body weight per day. In one embodiment, the dosage or aggregate dosage of noribogaine, noribogaine derivative, or salt or solvate thereof is about 1 mg/kg body weight per day.

In one embodiment, the dosage or aggregate dosage of noribogaine, noribogaine derivative, or salt or solvate thereof is between 70 mg and 150 mg. In one embodiment, the dosage or aggregate dosage of noribogaine, noribogaine derivative, or salt or solvate thereof is between 75 mg and 150 mg. In one embodiment, the dosage or aggregate dosage of noribogaine, noribogaine derivative, or salt or solvate thereof is between 80 mg and 140 mg. In one embodiment, the dosage or aggregate dosage of noribogaine, noribogaine derivative, or salt or solvate thereof is between 90 mg and 140 mg. In one embodiment, the dosage or aggregate dosage of noribogaine, noribogaine derivative, or salt or solvate thereof is between 90 mg and 130 mg. In one embodiment, the dosage or aggregate dosage of noribogaine, noribogaine derivative, or salt or solvate thereof is between 100 mg and 130 mg. In one embodiment, the dosage or aggregate dosage of noribogaine, noribogaine derivative, or salt or solvate thereof is between 110 mg and 130 mg.

In another embodiment, there is provided a unit dose of noribogaine, noribogaine derivative, or salt or solvate thereof which is about 120 mg per dose. It being understood that the term "unit dose" means a dose sufficient to provide therapeutic results whether given all at once or serially over a period of time.

In some embodiments, the patient is administered an initial dose of noribogaine, noribogaine derivative, or pharmaceutically acceptable salt or solvate thereof, followed by one or more additional doses. In one embodiment, such a dosing regimen provides an average serum concentration of noribogaine of 50 ng/mL to 180 ng/mL. In one embodiment, the one or more additional doses maintain an average serum concentration of 50 ng/mL to 180 ng/mL over a period of time.

In one embodiment, administration of noribogaine or derivative thereof comprises:

i) administering an initial dose of noribogaine, noribogaine derivative, or pharmaceutically acceptable salt or solvate thereof, wherein the initial dose provides an average serum concentration of 50 ng/mL to 180 ng/mL; and ii) administering at least one additional dose of noribogaine, noribogaine derivative, or pharmaceutically acceptable salt or solvate thereof, such that the at least one additional dose maintains the average serum concentration of 50 ng/mL to 180 ng/mL.

In some embodiments, the initial dose of noribogaine, noribogaine derivative, or salt or solvate thereof is from 75 mg to 120 mg. In one embodiment, the initial dose is about 75 mg. In one embodiment, the initial dose is about 80 mg. In one embodiment, the initial dose is about 85 mg. In one embodiment, the initial dose is about 90 mg. In one embodiment, the initial dose is about 95 mg. In one embodiment, the initial dose is about 100 mg. In one embodiment, the initial dose is about 105 mg. In one embodiment, the initial dose is about 110 mg. In one embodiment, the initial dose is about 115 mg. In one embodiment, the initial dose is about 120 mg.

In some embodiments, the one or more additional doses are lower than the initial dose. In one embodiment, the one or more additional doses are from 5 mg to 50 mg. In one embodiment, the one or more additional doses may or may not comprise the same amount of noribogaine, noribogaine derivative, or salt or solvate thereof. In one embodiment, at least one additional dose is about 5 mg. In one embodiment, at least one additional dose is about 10 mg. In one embodiment, at least one additional dose is about 15 mg. In one embodiment, at least one additional dose is about 20 mg. In one embodiment, at least one additional dose is about 25 mg. In one embodiment, at least one additional dose is about 30 mg. In one embodiment, at least one additional dose is about 35 mg. In one embodiment, at least one additional dose is about 40 mg. In one embodiment, at least one additional dose is about 45 mg. In one embodiment, at least one additional dose is about 50 mg.

In one embodiment, the one or more additional doses are administered periodically. In one embodiment, the one or more additional doses are administered every 4 hours. In one embodiment, the one or more additional doses are administered every 6 hours. In one embodiment, the one or more additional doses are administered every 8 hours. In one embodiment, the one or more additional doses are administered every 10 hours. In one embodiment, the one or more additional doses are administered every 12 hours. In one embodiment, the one or more additional doses are administered every 18 hours. In one embodiment, the one or more additional doses are administered every 24 hours. In one embodiment, the one or more additional doses are administered every 36 hours. In one embodiment, the one or more additional doses are administered every 48 hours.

In one embodiment, the noribgaine is administered orally, parenterally, by infusion or transdermally. These routes of administration are discussed in further detail in subsection 3 titled "Routes of Administration."

In certain embodiments of the present invention, noribogaine is administered to treat the behavioral addiction phase in an amount that achieves a serum concentration that is substantially less than that for treating the acute addiction stage. Preferably, behavioral addiction can be treated by a dosing of from 5 to 70% of the dosing provided in the acute addiction phase. In treating behavioral addiction, the dosing of noribogaine can be continuous or intermittent depending on the needs of the patient. In some cases, the patient may be initially treated with a continuous dosing regimen and then switched to an intermittent dosing.

In some embodiments, the therapeutic dose of noribogaine, noribogaine derivative, or salt or solvate thereof is a tapered dosing over a period of time, during which the patient is detoxified, for example, without suffering significant acute withdrawal symptoms. Without being bound by theory, it is believed that tapering will allow the full therapeutic effect of noribogaine with less prolongation of the QT interval. Tapering involves administration of one or more subsequently lower doses of noribogaine over time. For example, in some embodiments, the first tapered dose is 50% to 95% of the first or original dose. In some embodiments, the second tapered dose is 40% to 90% of the first or original dose. In some embodiments, the third tapered dose is 30% to 85% of the first or original dose. In some embodiments, the fourth tapered dose is 20% to 80% of the first or original dose. In some embodiments, the fifth tapered dose is 10% to 75% of the first or original dose.

Dosage and Routes of Administration

The compositions, provided herein or known, suitable for administration in accordance with the methods provide herein, can be suitable for a variety of delivery modes including, without limitation, oral and transdermal delivery. Compositions suitable for internal, pulmonary, rectal, nasal, vaginal, lingual, intravenous, intraarterial, intramuscular, intraperitoneal, intracutaneous and subcutaneous routes may also be used. A particularly suitable composition comprises a composition suitable for a transdermal route of delivery in which the noribogaine is applied as part of a cream, gel or, preferably, patch (for examples of transdermal formulations, see U.S. Pat. Nos. 4,806,341; 5,149,538; and 4,626,539, each of which are incorporated herein by reference). Other dosage forms include tablets, capsules, pills, powders, aerosols, suppositories, parenterals, and oral liquids, including suspensions, solutions and emulsions. Sustained release dosage forms may also be used. All dosage forms may be prepared using methods that are standard in the art (see e.g., Remington's Pharmaceutical Sciences, 16th ed., A. Oslo editor, Easton Pa. 1980).

Noribogaine can also be used in conjunction with any of the vehicles and excipients commonly employed in pharmaceutical preparations, e.g., talc, gum Arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerine and the like. Parenteral compositions containing noribogaine may be prepared using conventional techniques that may include sterile isotonic saline, water, 1,3-butanediol, ethanol, 1,2-propylene glycol, polyglycols mixed with water, Ringer's solution, etc.

Kit of Parts

One aspect of the present invention is directed to a kit of parts comprising a composition as disclosed herein and a means for administering the composition to a patient in need thereof. The means for administration to a patient can include, for example, any one or combination of a transdermal patch, a syringe, a needle, an IV bag comprising the composition, a vial comprising the composition, etc. For example, a kit can comprise any of the following (a) one or more doses of noribogaine; (b) reagents and/or devices for the administration of noribogaine; (c) one or more doses of morphine; (d) reagents and/or devices for the administration of morphine (e) reagents and/or devices for measuring methadone (f) reagents and/or devices for measuring noribogaine. Such a kit may contain suitable instructions.

EXAMPLES

The following Examples are intended to further illustrate certain embodiments of the disclosure and are not intended to limit its scope.

Example 1: Negative Interactions Between Methadone and Noribogaine

Overview

Administration of noribogaine is proposed for the treatment of addiction. Methadone is commonly taken both for pain relief and as part of the treatment of addiction, especially as a replacement for more addictive opiates and opioids such as heroin and oxycodone. Accordingly, the population who are most likely to be administered ibogaine are more likely than average to also be exposed to methadone. The objective of this study was to evaluate the potential adverse effects that may result following oral administration of noribogaine and methadone. Rats were used for evaluating the toxic effects because there is a large historical database of rat toxicology studies and rats have been used in prior toxicology studies with noribogaine. The number of animals selected for this study was considered to be the minimum number required to achieve biological and statistical significance based on 1) the study design and 2) the characteristics of the test article.

Oral doses for the test article and interaction article were selected as the routes of administration since both drugs are orally bioavailable, oral administration is convenient, in practice for both drugs, and typically preferred by human patients over injection. It is expected that similar results would be obtained with injection.

TABLE 1

| | Materials and methods. |
|---|---|
| Test System | One hundred and twenty male Sprague Dawley rats were randomly assigned to Groups 1 to 12 (10/group). Animals were received from Charles River Breeding Labs. Animals were approximately 8-10 weeks old and weighed 258-349 g on SD 1 and were identified by ear tags. |
| Feed | Certified Global Harlan Teklad 2018 Diet (pellets) was provided ad libitum. Animals were fasted overnight prior to dosing with both noribogaine and methadone. Food was returned 2 ± 0.5 h following administration of methadone. |
| Water | Water was provided ad libitum via automatic system. |
| Environment | Animals were individually housed in polycarbonate cages suspended on stainless steel racks. The animals were transferred to stainless steel caging with wire mesh bottoms and a drop pan within three days of dosing. Each cage was affixed with a cage card containing pertinent animal and study information. Animals were housed in a controlled environment. Enrichment (Nyla-Bone) was provided. |
| Noribogaine | Noribogaine hydrochloride stored in a refrigerator (2-8 C.) and protected from light upon receipt. The drug was administered a 35%:65% (v:v) mixture of 0.5% Tween 80 in 5% Dextrose in Water (v:v) and 1.5% (w:v) methylcellulose (400 cps) in Sterile Water for Injection (SWFI), USP, respectively. Stored at ambient temperature (16-26° C.). |
| Methadone | Methadone hydrochloride stored at 16-26° C. For administration, was dissolved in sterile water and stored at ambient temperature. |

Noribogaine in carrier was prepared once. The carrier was prepared by combining an appropriate amount of Tween 80 with 5% Dextrose in Water to prepare a 0.5% v:v solution. The solution was mixed well and stored at 2-8° C. An appropriate amount of methylcellulose was added over approximately 1 minute to boiling SWFI with vigorous mixing, and stored at room temperature to prepare a 1.5% (w:v) suspension, and allowed to cool. It was then formulated to achieve the desired dosage. The correction factor was 1.12 which was based on the hydrochloride salt form of noribogaine. The appropriate amount of noribogaine article was weighed and the carrier solution prepared above was added to provide 35% of the total final volume. The resulting suspension was stirred for at least 30 minutes, the suspension of methylcellulose in water was added to prepare the final total volume, and the suspension was stirred for at least another 30 minutes. The formulation was stored at 2-8° C. and protected from light prior to dosing.

Methadone was mixed in sterile water to the appropriate amount and 2-8° C. and protected from light prior to dosing.

Dosing

Each animal was weighed, and each drug was administered orally at 10 mL/kg of body weight.

Observations

TABLE 2

| | Animal Observations |
|---|---|
| Procedure | Frequency of Testing |
| Cageside Observations | ≥2 Daily |

TABLE 2-continued

| | Animal Observations |
|---|---|
| Procedure | Frequency of Testing |
| Physical Examinations | Prior to administration of each test/test article vehicle dose |
| Postdose (Test Article and Interaction Article) Observations | After test article or its vehicle: Continuously for the first 30 ± 5 min and then at 1 hr ± 10 min intervals until dosing with the interaction article After methadone or its vehicle (which occurred at 4 ± 0.5 hr post administration of the test article or its vehicle): Continuously for the first 60 ± 5 min immediately following methadone or its vehicle, and at 15 ± 5 min intervals for 2 subsequent hours |
| Body Weights | Prior to administration of each test article/vehicle dose |

On study day 4, all surviving animals were euthanized by carbon dioxide inhalation followed by exsanguination and discarded without necropsy. Animals that were found dead/moribund killed were necropsied as soon as possible after the time of death or discovery and checked for gavage error. No observations were noted and no tissues were collected or preserved; therefore, no discussion of the unscheduled deaths is presented in the results section.

Data Collection and Record Retention

Electronic data collection, including randomization, dose formulations and dispensing, dosing, animal husbandry, environmental enrichment, clinical, cageside, and postdose observations, and body weights was performed using Provantis™ Version 8 (Instem LSS, Limited; Stone, UK).

Results

Mortality

TABLE 3

| | | | Mortality | | | |
|---|---|---|---|---|---|---|
| Treatment Group Number | Noribogaine Dosage (mg/kg) | Methadone Dosage (mg/kg) | Number Dosed | Number Dead after Methadone | % Dead after Methadone | Time to Death after Methadone hh:mm |
| 1 | 0 | 0 | 10 | 0 | 0 | — |
| 2 | 0 | 1 | 10 | 0 | 0 | — |
| 3 | 0 | 3 | 10 | 1 | 10 | 1:3 |
| 4 | 0 | 5 | 10 | 3 | 30 | 0:55-4:17 |

TABLE 3-continued

Mortality

| Treatment Group Number | Noribogaine Dosage (mg/kg) | Methadone Dosage (mg/kg) | Number Dosed | Number Dead after Methadone | % Dead after Methadone | Time to Death after Methadone hh:mm |
|---|---|---|---|---|---|---|
| 5 | 50 | 0 | 10 | 0 | 0 | — |
| 6 | 50 | 1 | 10 | 0 | 0 | — |
| 7 | 50 | 3 | 10 | 6 | 60 | 1:45-4:05 |
| 8 | 50 | 5 | 10 | 9 | 90 | 0:40-4:01 |
| 9 | 150 | 0 | 10 | 0 | 0 | — |
| 1 | 150 | 1 | 10 | 6 | 60 | 0:25-1:15 |
| 1 | 150 | 3 | 10 | 1 | 100 | 0:10-2:00[a] |
| 1 | 150 | 5 | 10 | 10 | 100 | 0:22-0:47 |
| 2 | | 0 | | | | |

[a]Animal 11982 (11 m) was found dead on SD 2 at the morning mortality check; hence, the exact time of death is not available and so the range of 0:10-2:00 is for 9 animals.

There was no mortality associated with administration of noribogaine at doses of 0, 50, and 150 mg/kg followed by the interaction article vehicle. Mortality occurred in most groups receiving methadone alone or in combination with noribogaine; the exception was Group 2 in which no mortality occurred following a 10 mg/kg dose of methadone without prior administration of noribogaine. The lowest incidence of mortality occurred in those groups that received methadone alone (Treatment Groups 1-4); the mortality rate was 0, 10, and 30% at doses of 10, 30, and 50 mg/kg, respectively. When animals were pretreated with noribogaine the mortality rate increased and occurred at lower methadone doses when compared to the mortality rates following administration of methadone alone. For example in the treatment groups that received 150 mg/kg of noribogaine prior to methadone (Treatment Groups 9-12), 60%, 100% and 100% of the rats given 10, 30 and 50 mg/kg of methadone, respectively died during following dosing; there were no deaths in rats given 150 mg/kg of noribgaine alone. The methadone $LD_{50}$ was 68.24 mg/kg (confidence interval 63.58-73.25 mg/kg), 29.70 mg/kg (confidence interval 25.65-34.38 mg/kg), and 8.86 mg/kg (confidence interval 3.49-22.51 mg/kg) after 0, 50, and 150 mg/kg of noribogaine, respectively. Thus the data show that an interaction exists between methadone and noribogaine such that the lethality of methadone is increased when given with noribogaine.

Animal Disposition, Physical Examinations, Cageside, and Postdose Observations Noribogaine Following administration of noribogaine the following were observed: slight ataxia, salivation (slight or severe), and hunched posture. These observations persisted for up to 4 hours following dosing with a greater percentage of animals with observations of ataxia and salivation following a 150 mg/kg dose of noribogaine than at a dose of 50 mg/kg (60-70% versus 30-40%, respectively). The observations of ataxia and salivation were considered to be adverse because they indicate a potential effect on the central nervous system (CNS) In addition to the observation of salivation, ataxia, and hunched posture a few animals exhibited languid behavior and tremors involving the entire body approximately 5 hours following noribogaine at 50 mg/kg which are potentially CNS-related and adverse. Salivation, languid behavior, and ataxia were also noted approximately 5 hours following noribogaine at 150 mg/kg and a single animal exhibited rapid respirations. However, there were no observations of body tremors.

Methadone

Observations of slight ataxia, salivation, hunched posture, and languid behavior occurred within one hour following administration of methadone alone at doses of 10 and 30 mg/kg. The ataxia, salivation and languid behavior indicate a potential effect on the central nervous system and are adverse, and the ataxia and languid behavior are expected pharmacological effects of an opiate. Following administration of methadone alone at 50 mg/kg the animals became prostrate, had tremors, shallow respirations, and in some cases were severely languid with hunched posture. These observations were adverse because they are indicative of opiate overdosage and because mortality occurred in one animal 55 min following the dose of methadone at 50 mg/kg.

Methadone with Noribogaine

Methadone when administered at 10 mg/kg following noribogaine at 50 mg/kg resulted in ataxia, languid behavior, salivation, and hunched posture at incidence rates similar to controls which were not dosed with methadone. Increasing the methadone dose to 30 mg/kg resulted in the same observations but also resulted in observations of labored breathing, prostration, and stiffening of the body (most likely catalepsy). Mortality also occurred that was not observed following administration of methadone alone at this dose. The frequency of these observations (including mortality) increased following noribogaine at 50 mg/kg and methadone at 50 mg/kg when compared to administration of methadone alone 50 mg/kg.

Administration of methadone at 10 mg/kg following noribogaine at 150 mg/kg resulted in ataxia, languid behavior, salivation, and hunched posture at incidence rates that were greater than that of controls which were not dosed with methadone, and there was an increase in mortality. Increasing the dose of methadone to 30 mg/kg also resulted in observations of ataxia, languid behavior, salivation, and hunched posture at incidence rates that were greater than that of controls which were not dosed with methadone but were also greater than in animals dosed with noribogaine at 150 mg/kg followed by methadone at 10 mg/kg. In addition, observations of labored breathing, prostration, tremors of the whole body, and mortality also occurred that were not observed following methadone alone at 10 mg/kg. The frequency of these observations following methadone at 50 mg/kg following noribogaine at 150 mg/kg was similar to that following methadone at 30 mg/kg when given after 150 mg/kg of noribogaine.

Adverse observations associated with administration of noribogaine alone persisted for approximately 6.5 to 7 hours following dosing which correlates with the reported long half-life of noribogaine following oral administration. Observations of slight languid behavior persisted through 1.75 hours following administration of methadone alone at 10 mg/kg but adverse observations associated with methadone at doses of 30 and 50 mg/kg persisted through 3 hours following the methadone dose. Following noribogaine at 50 mg or 150 mg/kg and methadone at 10, 30, and 50 mg/kg adverse observations resolved over times similar to those observed for noribogaine when given alone at doses of 50 and 150 mg/kg.

CONCLUSIONS

The purpose of the study was to evaluate the potential adverse effects that may result when noribogaine (test article) was administered orally prior to the oral administration of methadone (interaction article) to male Sprague Dawley rats.

This study tested oral doses of 50 and 150 mg/kg noribogaine (as noribogaine hydrochloride); the doses were selected based on the data supplied by the Sponsor. The noribogaine dose was administered 4 h±0.5 h prior to administration of methadone which is within the range corresponding to the $T_{max}$ of oral noribogaine in rats. Methadone oral doses of 10, 30, and 50 mg/kg were administered to facilitate detection of possible potentiating effects of noribogaine on methadone lethality.

In conclusion, slight ataxia, salivation (slight or severe), and hunched posture occurred following noribogaine doses of 50 and 150 mg/kg. Observations of slight ataxia, salivation, hunched posture, and languid behavior occurred when methadone alone was given at doses of 10 and 30 mg/kg and prostration, tremors, and shallow respirations were observed following a methadone dose of 50 mg/kg. Dose-dependent mortality occurred at methadone doses of 30 and 50 mg/kg. When methadone was administered following administration of noribogaine there was a dose-dependent increase in severity and frequency of ataxia, languid behavior, salivation, labored/shallow respirations, prostration, and hunched posture, and the appearance body stiffening (possibly catalepsy), and a dose-dependent increase in mortality. The methadone $LD_{50}$ was 68.24 mg/kg (confidence interval 63.58-73.25 mg/kg), 29.70 mg/kg (confidence interval 25.65-34.38 mg/kg), and 8.86 mg/kg (confidence interval 3.49-22.51 mg/kg) after 0, 50, and 150 mg/kg of noribogaine, respectively. These data show that oral administration of noribogaine at doses of 50 and 150 mg/kg potentiates the mortality associated with oral administration of methadone. Accordingly, there is a negative interaction between methadone and noribogaine such that the lethality of methadone is increased when given with noribogaine.

Example 2: Pharmacokinetics and Pharmacodynamics of Noribogaine in Humans

Thirty-six healthy, drug-free male volunteers, aged between 18-55 years, were enrolled in and completed the study. This was an ascending single-dose, placebo-controlled, randomized double blind, parallel group study. Mean (SD) age was 22.0 (3.3) years, mean (SD) height was 1.82 (0.08) m, and mean (SD) weight was 78.0 (9.2) kg. Twenty-six subjects were Caucasian, 3 were Asian, 1 Maori, 1 Pacific Islander, and 5 Other. The protocol for this study was approved by the Lower South Regional Ethics Committee (LRS/12/06/015), and the study was registered with the Australian New Zealand Clinical Trial Registry (AC-TRN12612000821897). All subjects provided signed informed consent prior to enrolment, and were assessed as suitable to participate based on review of medical history, physical examination, safety laboratory tests, vital signs and ECG.

Within each dose level, 6 participants were randomized to receive noribogaine and 3 to receive placebo, based on a computer-generated random code. Dosing began with the lowest noribogaine dose, and subsequent cohorts received the next highest dose after the safety, tolerability, and blinded pharmacokinetics of the completed cohort were reviewed and dose-escalation approved by an independent Data Safety Monitoring Board. Blinded study drug was administered as a capsule with 240 ml of water after an overnight fast of at least 10 hours. Participants did not receive any food until at least 5 hours post-dose. Participants were confined to the study site from 12 hours prior to drug administration, until 72 hours post-dose, and there were subsequent outpatient assessments until 216 hours post-dose.

Blood was obtained for pharmacokinetic assessments pre-dose and then at 0.25, 0.5, 0.75, 1.0, 1.25, 1.5, 2, 2.5, 3, 3.5, 4, 4.5, 5, 5.5, 6, 7, 8, 10, 12, 14, 18, 24, 30, 36, 48, 60, 72, 96, 120, 168 and 216 hours post-dose. Samples were centrifuged and plasma stored at −70° C. until analyzed. Block 24 hour urine collections were obtained following study drug administration for the 30 and 60 mg cohorts. Aliquots were frozen at −20° C. until analyzed.

Pulse oximetry and capnography data were collected continuously using a GE Carescape B650 monitoring system from 2 hours prior to dosing and until six hours after dosing, and thereafter at 12, 24, 48 and 72 hours post-dosing. Additional oximetry data were collected at 120, 168 and 216 hours. Pupillary miosis was assessed by pupillometry. Dark-adapted pupil diameter was measured in triplicate using a Neuroptics PLR-200 pupillometer under standardized light intensity (<5 lux) pre-dose, and at 2, 4, 6, 12, 24, 48, 72, 96, 120, 168 and 216 hours post-dosing.

Plasma noribogaine concentrations were determined in the 3 mg and 10 mg dose groups using a validated, sensitive LCMSMS method. Sample preparation involved double extraction of basified plasma samples with tert-butyl methyl ether, drying the samples under a stream of nitrogen and reconstitution of sample with acetonitrile:B.P. water (5:95, v/v) containing 0.1% (v/v) formic acid. The compounds were separated by a 150×2.0 mm Luna 5 μm C18 column and detected with a triple-quadrupole API 4000 or 5000 mass spectrometer using electrospray ionization in positive mode and multiple reaction monitoring. Noribogaine-$d_4$ was used as the internal standard. The precursor-product ion transition values for noribogaine were m/z 297.6→122.3, and for the internal standard noribogaine-$d_4$ m/z 301.1→122.2. Analyst® software was used for data acquisition and processing. The ratio of the peak area of noribogaine to the internal standard noribogaine-$d_4$ was used for calibration and measurement of the unknown concentration of noribogaine. The lower limit of quantification (LLOQ) was 0.025 ng/ml noribogaine. The calibration curve was between 0.025 and 25.600 ng/ml noribogaine. Mobile phase A was acetonitrile:B.P. water (5:95, v/v) containing 0.1% (v/v) formic acid, and mobile phase B was acetonitrile:B.P. water (95:5, v/v) containing 0.1% (v/v) formic acid. Total run time was 6 minutes. Binary flow: Initial concentration was 8% mobile phase B; hold at 8% mobile phase B for 0.5 minutes and linear rise to 90% mobile phase B over 1.5 minutes; hold at 90% mobile phase B for 1 minute and then drop back to 8% mobile phase B over 0.01 minute. Equilibrate system for 3 minutes. Total run time was 6 minutes.

Within- and between-day assay precision was <9%, and within- and between-day assay accuracy was <9%.

Plasma noribogaine concentrations were determined in the 30 mg and 60 mg dose groups using a validated, sensitive LCMSMS method. Sample preparation involved deproteinization of plasma samples with acetonitrile and dilution of sample with 0.1% (v/v) formic acid. The compounds were separated by a 150×2.0 mm Luna 5 μm C18 column and detected with a triple-quadrupole API 4000 or 5000 mass spectrometer using electrospray ionization in positive mode and multiple reaction monitoring. Noribogaine-$d_4$ was used as the internal standard. The precursor-product ion transition values for noribogaine were m/z 297.6→122.3, and for the internal standard noribogaine-$d_4$ m/z 301.1→122.2. Analyst® software was used for data acquisition and processing. The ratio of the peak area of noribogaine to the internal standard noribogaine-$d_4$ was used for calibration and measurement of the unknown concentration of noribogaine. The LLOQ was 0.50 ng/ml noribogaine. The calibration curve was between 0.50 and 256.00 ng/ml noribogaine. Mobile phase was the same as method A, and binary flow was also the same as method A. The within- and between-day assay precision was <9%, and the within- and between-day assay accuracy was <9%.

Plasma noribogaine glucuronide concentrations were determined in the 30 mg and 60 mg dose groups using a validated sensitive LCMSMS method. Sample preparation involved deproteinization of plasma samples with acetonitrile, drying the samples under a stream of nitrogen and reconstitution of sample with acetonitrile: B.P. water (5:95, v/v) containing 0.1% (v/v) formic acid. The compounds were separated by a 150×2.0 mm Luna 5 μm C18 column and detected with a triple-quadrupole API 4000 or 5000 mass spectrometer using electrospray ionization in positive mode and multiple reaction monitoring. Noribogaine-$d_4$ was used as the internal standard. The precursor-product ion transition values for noribogaine glucuronide were m/z 472.8→297.3, and for the internal standard noribogaine-$d_4$ m/z 301.1→122.2. Analyst® software was used for data acquisition and processing. The ratio of the peak area of noribogaine glucuronide to the internal standard noribogaine-$d_4$ was used for calibration and measurement of the unknown concentration of noribogaine. The LLOQ was 0.050 ng/ml noribogaine glucuronide. The calibration curve was between 0.050 and 6.400 ng/ml noribogaine glucuronide. Mobile phases was the same as method A. Binary flow: Initial concentration was 6% mobile phase B; hold at 6% mobile phase B for 0.5 minutes and linear rise to 90% mobile phase B over 2 minutes; hold at 90% mobile phase B for 1 minute and then drop back to 6% mobile phase B over 0.01 minute. Equilibrate system for 3.5 minutes. Total run time was 7 minutes. The within- and between-day assay precision was <11%, and the within- and between-day assay accuracy was <10%.

Urine noribogaine and noribogaine glucuronide concentrations were determined in the 30 mg and 60 mg dose groups using a validated sensitive LCMSMS method. Sample preparation involved deproteinization of urine samples with acetonitrile and dilution of the sample with 0.1% (v/v) formic acid. The compounds were separated by a 150×2.0 mm Luna 5 μm C18 column and detected with a triple-quadrupole API 5000 mass spectrometer using electrospray ionization in positive mode and multiple reaction monitoring. Noribogaine-$d_4$ was used as the internal standard. The precursor-product ion transition values for noribogaine were m/z 297.6→122.3, noribogaine glucuronide m/z 472.8→297.3, and for the internal standard noribogaine-$d_4$ m/z 301.1→122.2. Analyst® software was used for data acquisition and processing. The ratios of the peak area of noribogaine and noribogaine glucuronide to the internal standard noribogaine-$d_4$ were used for calibration and measurement of the unknown concentration of noribogaine and its glucuronide. Assay LLOQ was 20.0 ng/ml for noribogaine and 2.0 ng/ml for noribogaine glucuronide. The calibration curve was between 20.0 and 5120.0 ng/ml noribogaine, and 2.0 and 512.0 ng/ml noribogaine glucuronide. Mobile phases were as described in method A, and binary flow as in method C. The within- and between-day assay precision was <13%, and within- and between-day assay accuracy was <12%.

Noribogaine and noribogaine glucuronide concentrations above the limit of quantification were used to calculate pharmacokinetic parameters using model-independent methods. The maximum plasma concentration (Cmax) and time to maximum plasma concentration (Tmax) were the observed values. Plasma concentration data in the post-distribution phase of the plasma concentration-time plot were fitted using linear regression to the formula ln C=ln Co−t.Kel, where Co was the zero-time intercept of the extrapolated terminal phase and Kel was the terminal elimination rate constant. The half-life ($t_{1/2}$) was determined using the formula $t_{1/2}$=0.693/Kel. The area under the concentration-time curve (AUC) from time zero to the last determined concentration-time point (tf) in the post distribution phase was calculated using the trapezoidal rule. The area under the curve from the last concentration-time point in the post distribution phase (Ctf) to time infinity was calculated from $AUC_{t-\infty}$=Ctf/Kel. The concentration used for Ctf was the last determined value above the LLOQ at the time point. The total $AUC_{0-\infty}$ was obtained by adding $AUC_{tf}$ and $AUC_{t-\infty}$. Noribogaine apparent clearance (CL/F) was determined using the formula CL/F=Dose/$AUC_{0-\infty}$, and apparent volume of distribution (Vd/F) was determined using the formula Vd/F=(CL/F)/Kel. Total urine noribogaine was the sum of both analytes.

Summary statistics (means, standard deviations, and coefficients of variation) were determined for each dose group for safety laboratory test data, ECG and pharmacokinetic parameters, and pharmacodynamic variables. Categorical variables were analysed using counts and percentages. Dose-proportionality of AUC and Cmax was assessed using linear regression. The effect of dose on pharmacodynamic parameter values over time was assessed using two-factor analysis of variance (ANOVA). Pairwise comparisons (with Tukey-Kramer adjustment) between each dose group to the placebo were conducted at each time point using the least squares estimates obtained from the ANOVA, using SAS Proc Mixed (SAS ver 6.0).

Results

Figure 2:
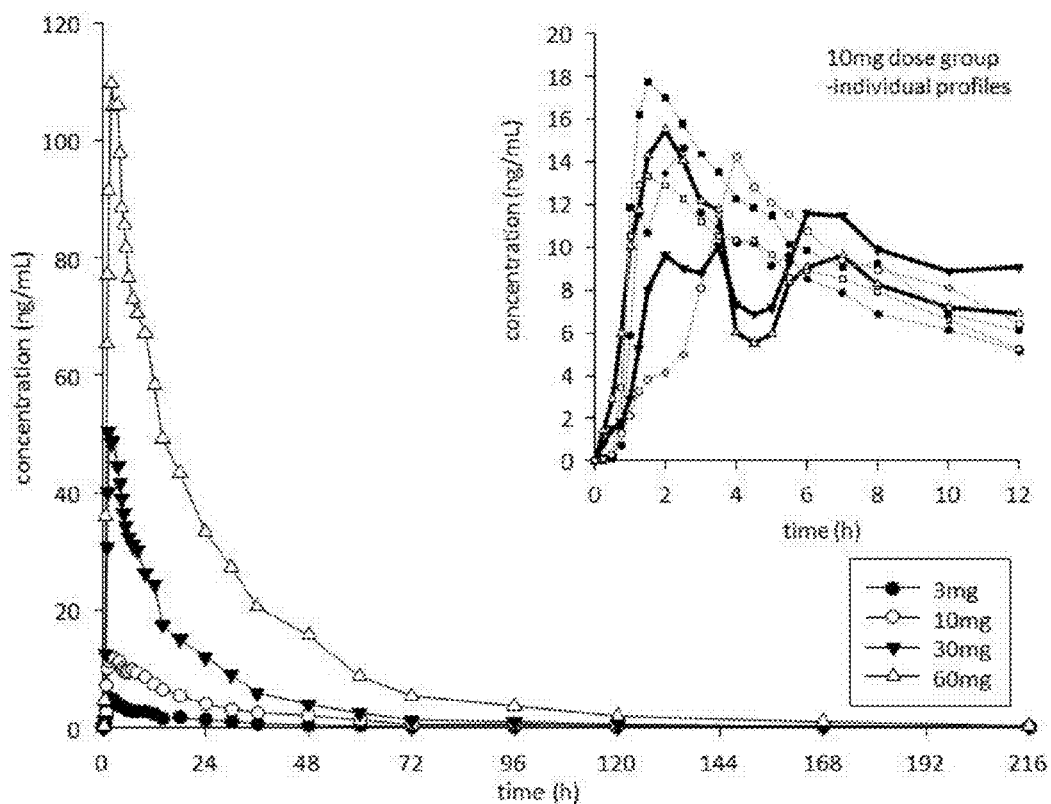
FIG. 2 represents mean noribogaine concentration-time profiles in healthy patients after single oral dosing with 3, 10, 30 or 60 mg doses. Inset: Individual concentration-time profiles from 0-12 h after a 10 mg dose.

Pharmacokinetics: Mean plasma concentration-time plots of noribogaine are shown in FIG. 2, and mean pharmacokinetic parameters are shown in Table 4.

TABLE 4

| | 3 mg (n = 6) (mean (SD)) | 10 mg (n = 6) (mean (SD)) | 30 mg (n = 6) (mean (SD)) | 60 mg (n = 6) (mean (SD) |
|---|---|---|---|---|
| Noribogaine | | | | |
| $AUC_{0-\infty}$ (hg · hr/ml) | 74.2 (13.1) | 254.5 (78.9) | 700.4 (223.3) | 1962.2 (726.5) |
| $AUC_{0-216}$ (ng · hr/ml) | 72.2 (13.2) | 251.4 (78.5) | 677.6 (221.1) | 1935.4 (725.4) |
| Cmax (ng/ml) | 5.2 (1.4) | 14.5 (2.1) | 55.9 (14.8) | 116.0 (22.5) |
| Tmax (hr) | 1.9 (0.6) | 2.9 (1.8) | 1.8 (0.6) | 2.4 (0.6) |
| $t_{1/2}$ (hr) | 40.9 (8.7) | 49.2 (11.5) | 27.6 (7.0)) | 29.1 (9.3) |
| Vd/F (L) | 2485.1 (801.5) | 3085.8 (1197.0) | 1850.8 (707.9) | 1416.8 (670.1) |
| CL/F (L/h) | 41.4 (7.0) | 42.3 (12.0) | 46.9 (16.4) | 34.0 (11.4) |
| Noribogaine glucuronide | | | | |
| $AUC_{0-\infty}$ (ng · hr/ml) | — | — | 25.8 (9.3) | 67.1 (21.9) |
| $AUC_{0-216}$ (ng · hr/ml) | — | — | 25.7 (9.1) | 65.0 (21.5) |
| Cmax (ng/ml) | — | — | 1.8 (0.6) | 4.1 (1.2) |
| Tmax (hr) | — | — | 3.0 (0.6) | 3.8 (1.2) |
| $t_{1/2}$(hr) | — | — | 20.6 (4.9) | 23.1 (3.0) |

Noribogaine was rapidly absorbed, with peak concentrations occurring 2-3 hours after oral dosing. Fluctuations in individual distribution-phase concentration-time profiles may suggest the possibility of enterohepatic recirculation (see highlighted individual 4-8 hour profiles in FIG. 2, insert). Both Cmax and AUC increased linearly with dose (Table 4, upper panel). Mean half-life estimates of 28-50 hours were observed across dose groups for noribogaine. Volume of distribution was extensive (1417-3086 L across dose groups).

Figure 3:
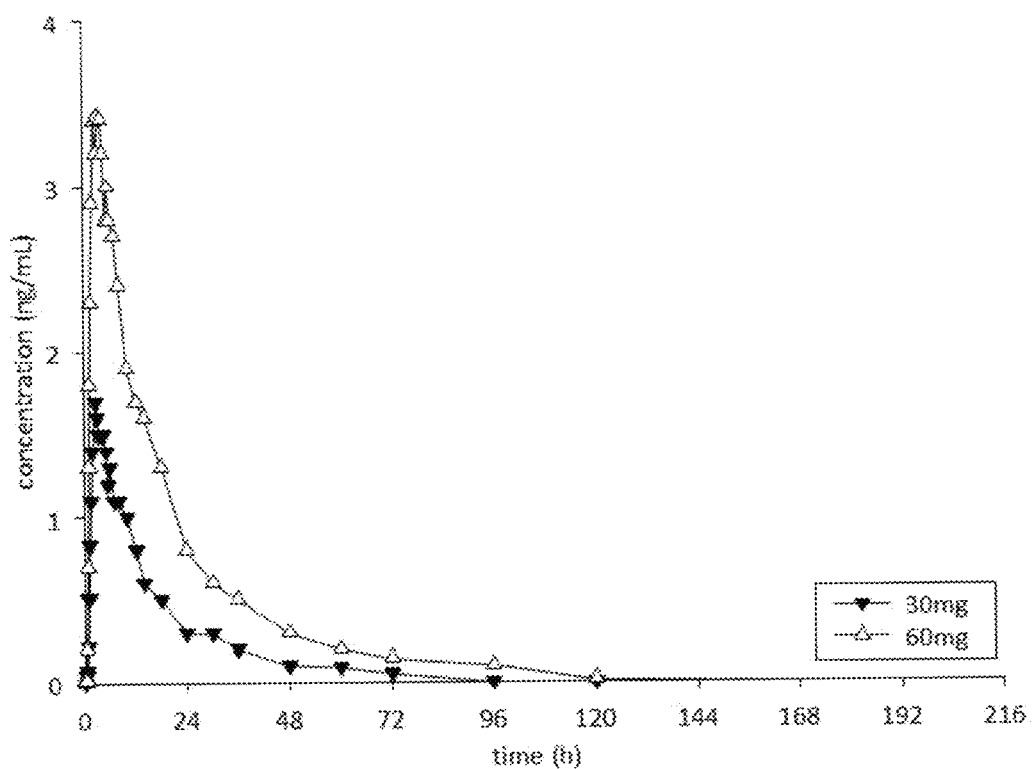
FIG. 3 represents mean plasma noribogaine glucuronide concentration-time profiles in healthy patients after single oral 30 or 60 mg doses.

Mean plasma noribogaine glucuronide concentration-time plots for the 30 mg and 60 mg dose group are shown in FIG. 3, and mean pharmacokinetic parameters are shown in Table 4, lower panel. Noribogaine glucuronide was detected in all subjects by 0.75 hours, with peak concentrations occurring 3-4 hours after noribogaine dosing. Mean half-life of 21-23 hours was estimated for plasma noribogaine glucuronide. The proportion of noribogaine glucuronide Cmax and AUC relative to noribogaine was 3-4% for both dose groups. Total urine noribogaine elimination was 1.16 mg and 0.82 mg for the 30 mg and 60 mg dose groups respectively, representing 3.9% and 1.4% of the doses administered.

Pharmacodynamics: There was no evidence of pupillary constriction in subjects dosed with noribogaine. No between-dose group differences in pupil diameter were detected over time. After adjusting for baseline differences, comparison of each dose group with placebo by ANOVA showed no statistically significant differences (p>0.9).

Noribogaine treatment showed no analgesic effect in the cold pressor test. Analgesic effect was assessed based on duration of hand immersion in ice water and on visual analog scale (VAS) pain scores upon hand removal from the water bath. For duration of hand immersion, after adjusting for baseline differences, comparison of each dose group with placebo by ANOVA showed no statistically significant differences (p>0.9). Similarly, for VAS pain scores, after adjusting for baseline differences, comparison of each dose group with placebo by ANOVA showed no statistically significant differences (p=0.17).

Example 3: Safety and Tolerability of Noribogaine in Humans

Safety and tolerability of noribogaine were tested in the group of volunteers from Example 2. Cold pressor testing was conducted in 1° C. water according to the method of Mitchell et al. (*J Pain* 5:233-237, 2004) pre-dose, 6, 24, 48, 72 and 216 hours post-dosing. Safety evaluations included clinical monitoring, recording of adverse events (AEs), safety laboratory tests, vital signs, ECG telemetry from −2 h to 6 h after dosing, and 12-lead electrocardiograms (ECGs) up to 216 hours post-dosing.

Results

A total of thirteen adverse events were reported by seven participants (Table 5). Six adverse events were reported by three participants in the placebo group, five adverse events were reported by two subjects in the 3 mg dose group, and one adverse event was reported by single subjects in the 10 mg and 30 mg dose groups, respectively. The most common adverse events were headache (four reports) and epistaxis (two reports). All adverse events were of mild-moderate intensity, and all resolved prior to study completion. There were no changes in vital signs or safety laboratory tests of note. In particular, there were no changes in oximetry or capnography, or changes in respiratory rate. There were no QTcF values >500 msec at any time. One subject dosed with 10 mg noribogaine had a single increase in QTcF of >60 msec at 24 hours post-dosing.

TABLE 5

| Dose (mg) | Mild | Moderate | Severe |
|---|---|---|---|
| Placebo | Blepharitis<br>Bruising<br>Dry Skin<br>Eye pain, nonspecific<br>Infection at cannula site | Epistaxis | — |
| 3 | Back pain<br>Dizziness<br>Epistaxis<br>Headache | Headache | — |

TABLE 5-continued

| Dose (mg) | Mild | Moderate | Severe |
| --- | --- | --- | --- |
| 10 | Headache | — | — |
| 30 | Headache | — | — |
| 60 | — | — | — |

Example 4: Efficacy of Noribogaine in Humans

The efficacy of noribogaine in humans was evaluated in opioid-dependent participants in a randomized, placebo-controlled, double-blind trial. Patients had been receiving methadone treatment as the opioid substitution therapy, but were transferred to morphine treatment prior to noribogaine administration. This was done to avoid negative noribogaine-methadone interactions that are not observed between noribogaine and methadone. See U.S. Provisional Application No. 61/852,485, filed Mar. 15, 2013, which is incorporated herein by reference in its entirety.

In the first cohort, six patients were orally administered a single dose of 60 mg noribogaine, and three patients received placebo. In the second cohort, five patients were orally administered a single dose of 120 mg noribogaine, and three patients received placebo. Treatment was administered 2 hours after last morphine dose and the time to resumption of morphine (opioid substitution treatment, OST) was determined. No adverse effects of noribogaine were observed in any of the participants, including no hallucinatory effects.

Figure 4:
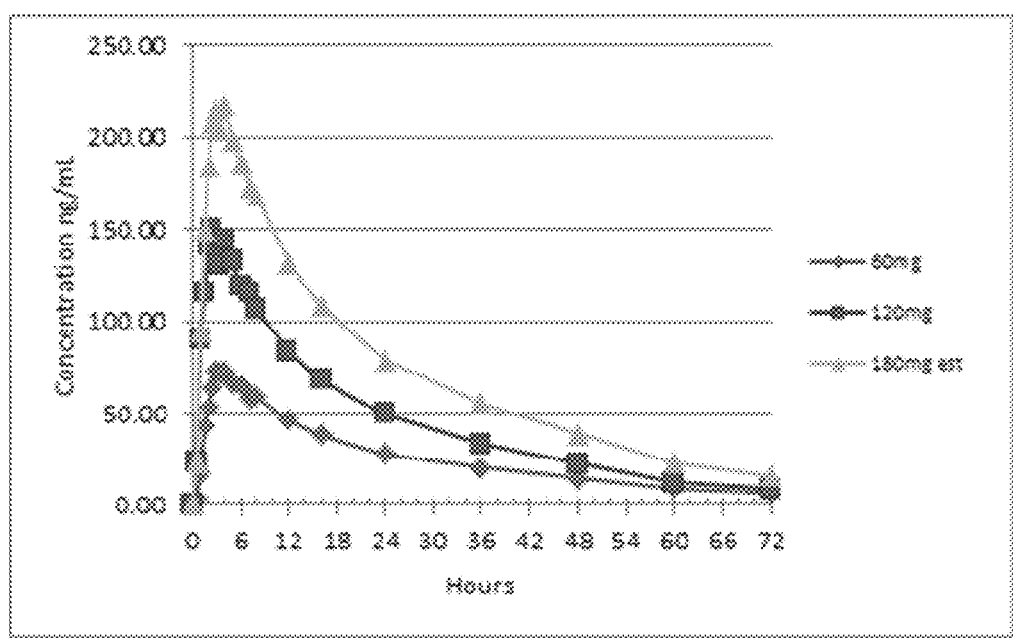
FIG. 4 illustrates the mean noribogaine concentration-time profile in opioid-addicted patients after a single oral 60 mg (diamonds) or 120 mg (squares) dose of noribogaine. Mean noribogaine concentration-time profile in opioid-addicted patients after single oral 180 mg dose of noribogaine (triangles) was estimated based on values for patients receiving 120 mg dose.

FIG. 4 indicates the serum noribogaine concentration over time. Serum concentrations for 180 mg dose (triangles) are estimated based on data from the 120 mg dose (squares).

Blinded Results

Figure 5A:
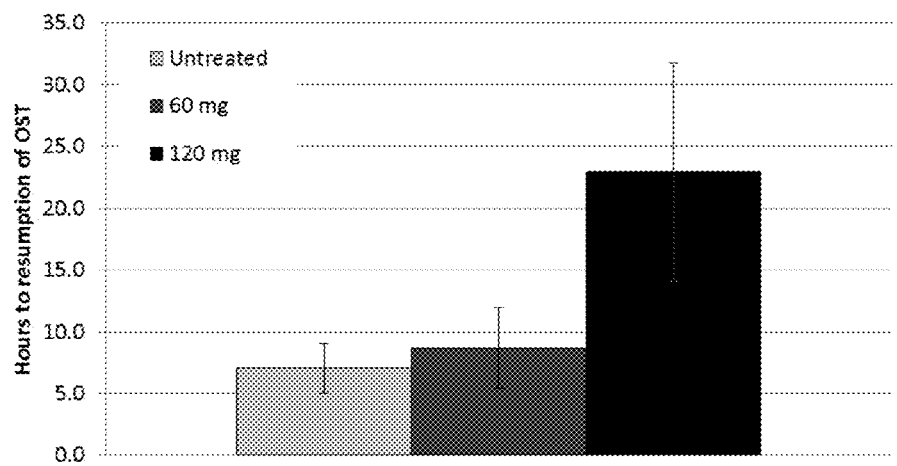
FIG. 5A illustrates hours to resumption of opioid substitution treatment in patients given no treatment (light gray bar), or a single oral dose of noribogaine or placebo (60 mg, dark gray bar; 120 mg, black bar). Error bars represent standard deviation.

Patients in the first cohort exhibited an average time to resumption of opioids after treatment with 60 mg noribogaine or placebo of approximately 8.7 hours, which is almost 2 hours longer than that reported for untreated patients in a similar study. Patients in the second cohort exhibited an average time to resumption of opioids after treatment with 120 mg noribogaine or placebo of approximately 22 hours. FIG. 5A indicates the average time to resumption of morphine for control (untreated, light gray bar), first cohort (dark gray bar) and second cohort (black bar). Mean prolongation of the QT interval was less than 10 ms for patients in the first cohort and was less than 40 ms in the second cohort.

Figure 5B:
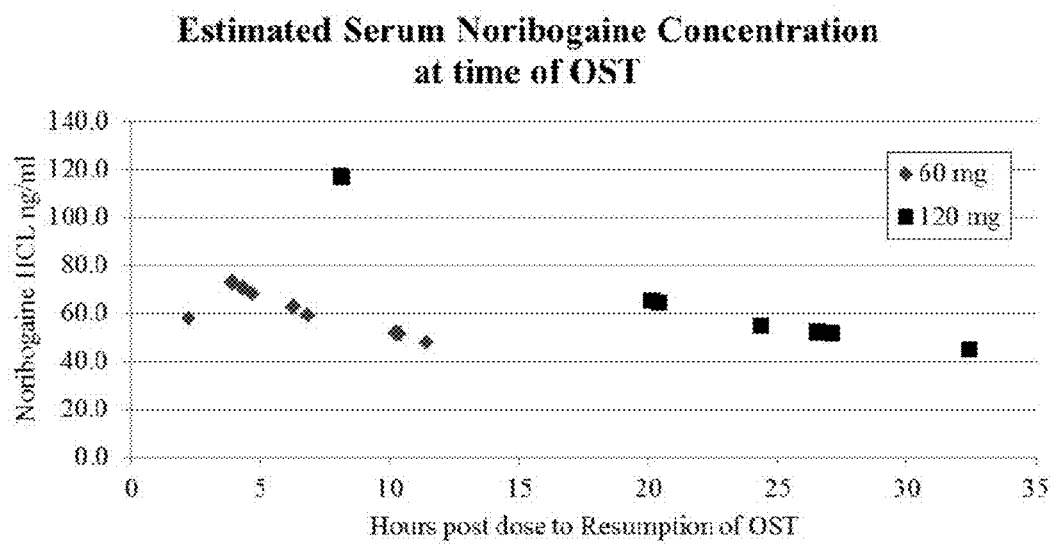
FIG. 5B illustrates the estimated serum noribogaine concentration in ng/mL at time of resumption of opioid substitution treatment (OST) in patients receiving single oral dose of noribogaine or placebo (60 mg, dark gray diamonds; 120 mg, black squares). Data is estimated based on the concentration-time profile in FIG. 4.

FIG. 5B indicates the estimated noribogaine concentration (based on the data from FIG. 4) at the time of resumption of morphine for each patient.

Figure 6A:
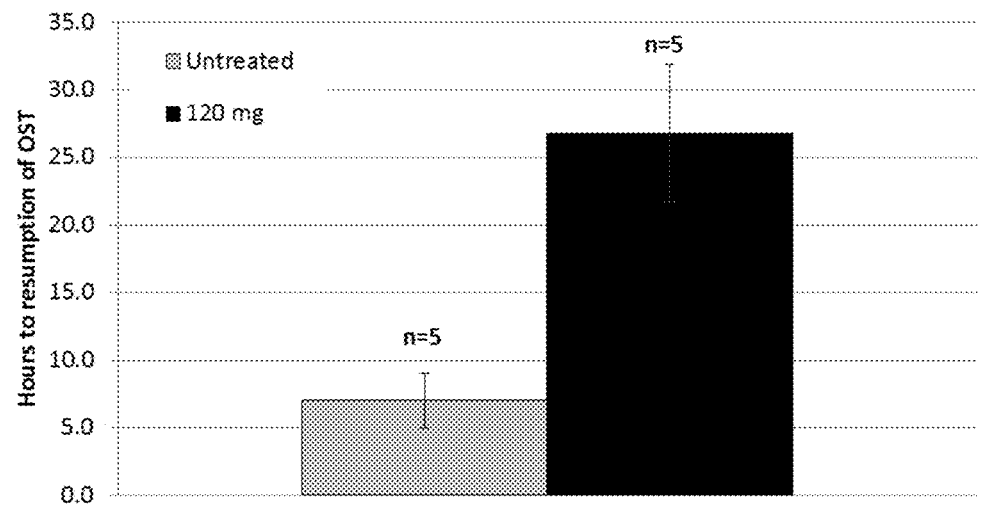
FIG. 6A illustrates imputed results of noribogaine treated patients wherein the results represent hours to resumption of OST in patients given no treatment (light gray bar), or a (imputed) single 120 mg dose of noribogaine (black bar). Error bars represent standard deviation.
Figure 6B:
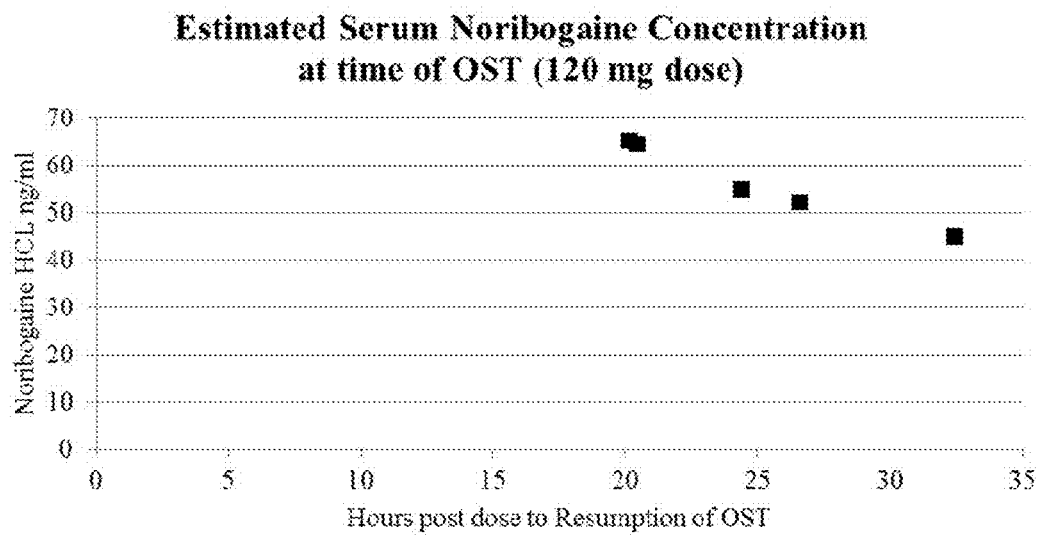
FIG. 6B illustrates imputed results of noribogaine treated patients wherein the results represent the estimated serum noribogaine concentration in ng/mL at time of resumption of OST in patients receiving a (imputed) single oral 120 mg dose of noribogaine (black squares). Data is estimated based on the concentration-time profile in FIG. 4.

Although the study was blinded, the three patients in the second cohort who received placebo were construed to be those patients exhibiting no prolongation of the QT interval. The average time to resumption of OST for the remaining five patients was determined to be approximately 26.8 hours, as indicated in FIG. 6A (black bar). FIG. 6B indicates the estimated noribogaine concentration (based on the data from FIG. 4) at the time of resumption of morphine for each (presumed) noribogaine-treated patient. FIG. 6B demonstrates that, as serum concentrations of noribogaine reach an estimated level of 50 to 60 ng/mL, significant withdrawal symptoms return such that the patient is forced to resume OST. At serum noribogaine levels above about 50 to 60 ng/mL, the patients did not exhibit withdrawal symptoms or those symptoms had not become acute.

Figure 7:
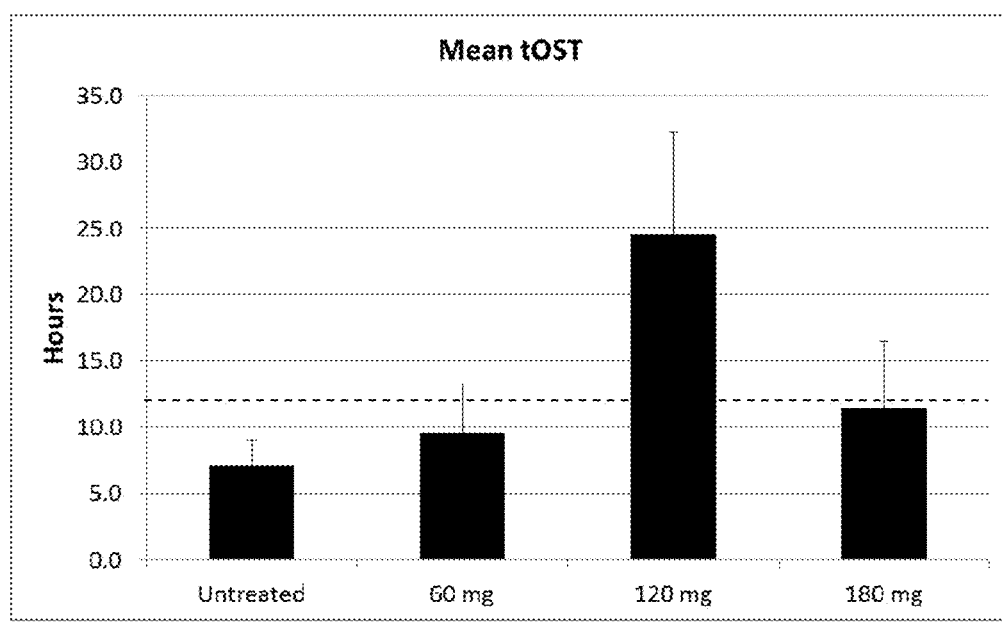
FIG. 7 illustrates imputed results of noribogaine treated patients wherein the results represent hours to resumption of OST in patients receiving a (imputed) single oral 60 mg, 120 mg or 180 mg dose of noribogaine, or no treatment. Dotted line represents average OST for placebo.

A third cohort of patients was administered 180 mg of noribogaine or placebo. Although the study was blinded, the 3 patients in the third cohort who received placebo were construed to be those patients exhibiting no prolongation of the QT interval. The average time to resumption of OST for the remaining 6 patients was determined to be approximately 11.4 hours, as shown in FIG. 7. This demonstrates that increasing the dose of noribogaine to 180 mg results in a shorter time to resumption of OST than observed in patients receiving 120 mg noribogaine (24.5 hours). Time to resumption of OST after treatment with 180 mg was still longer than untreated patients or those (putatively) administered 60 mg noribogaine (7 hours and 9.6 hours, respectively). It was similar to the time to resumption of OST observed in patients (putatively) administered placebo (dotted line, 11.8 hours).

Data shows therapeutic activity at all concentrations, albeit in an inverted-U curve. While not reported, QT interval is believed to increase in linear manner as dose is increased from 60 mg to 180 mg. At 180 mg, the change in the QT interval prolongation appears to be above 30 ms. Based on above data, it is believed that the therapeutic window for a single bolus dose of noribogaine is bound at the lower end by 50 mg and at the upper end by less than 180 mg. In particular, the therapeutic range in vivo appears to be between 50 ng/mL and 180 ng/mL.

What is claimed is:

1. A method for treating addiction in a patient in need thereof being administered methadone, the method comprising:
   (a) replacing methadone administration with another opioid for a period of time of at least one day such that the serum level of methadone is reduced; and thereafter
   (b) administering noribogaine, an ester thereof, or a pharmaceutically acceptable salt or solvate of each thereof to the patient at an amount of from about 60 mg to about 180 mg per day, wherein the patient's QT interval is maintained at less than about 500 ms.

2. The method of claim 1, wherein step (b) comprises:
   i) administering an initial dose of noribogaine, the ester thereof, or the pharmaceutically acceptable salt or solvate thereof, wherein the initial dose provides an average serum noribogaine concentration of 50 ng/mL to 180 ng/mL; and
   ii) administering at least one additional dose of noribogaine, the ester thereof, or the pharmaceutically acceptable salt or solvate thereof, such that the at least one additional dose maintains the average serum noribogaine concentration of 50 ng/mL to 180 ng/mL.

3. The method of claim 2, wherein the initial dose is from 50 mg to 120 mg.

4. The method of claim 2, wherein the at least one additional dose is from 5 mg to 50 mg.

5. The method of claim 2, wherein the at least one additional dose is administered from 6 hours to 24 hours after the initial dose.

6. The method of claim 2, wherein at least two additional doses are administered, and further wherein each additional dose is administered from 6 hours to 24 hours after the previous dose.

7. The method of claim 1, further comprising selecting an addicted patient who is prescreened to evaluate tolerance for prolongation of QT interval.

8. The method of claim 1, wherein the serum level of methadone is from about 3 μg/L to about 56 μg/L.

9. The method of claim 1, further comprising measuring the level of methadone or methadone metabolites in a bodily fluid from the patient.

10. The method of claim 1, wherein the opioid is morphine.

11. The method of claim 10, wherein the morphine is an extended-release morphine.

12. The method of claim 1, wherein the cessation of methadone administration occurs through a gradual reduction in the dose or frequency of administration of methadone.

13. The method of claim 1, wherein the period of time is at least 200 hours.

14. The method of claim 1, wherein the period of time is at least a week.

15. The method of claim 1, wherein all or substantially all of the drug is removed from the patient prior to step b).

16. The method of claim 1, wherein step (b) comprises:
i) administering an initial dose of noribogaine, the ester thereof, or the pharmaceutically acceptable salt or solvate thereof, wherein the initial dose is from 50 mg to 120 mg; and
ii) administering at least one additional dose of noribogaine, the ester thereof, or the pharmaceutically acceptable salt or solvate thereof, wherein the at least one additional dose is from 5 mg to 75 mg.

17. A method for treating addiction in a patient in need thereof, comprising: (a) determining the presence of a drug that interacts negatively with noribogaine in the patient, wherein the drug is methadone, a mu agonist, a drug which prolongs QT interval, or a drug that causes respiratory depression; (b) in a patient positive for the presence of the drug, replacing administration of the drug with another opioid for a period of time until all or substantially all of the drug is removed; and (c) to a patient negative for the drug, or from whom all or substantially all of the drug is removed, administering noribogaine, an ester thereof, or a pharmaceutically acceptable salt or solvate of each thereof at an amount of from about 60 mg to about 180 mg per day to treat said patient's addiction, wherein the patient's QT interval is maintained at less than about 500 ms during said treatment.

18. The method of claim 17, wherein the drug that interacts negatively with noribogaine is methadone.

19. The method of claim 17, wherein, prior to administration of noribogaine, the ester thereof, or the pharmaceutically acceptable salt or solvate thereof, the patient is placed in a controlled environment until the level of the drug in the patient is substantially zero.

20. The method claim 17, wherein the opioid is morphine.

21. A method of treating addiction in a patient in need thereof, comprising:
(a) administering a unit dose of noribogaine, an ester thereof, or a pharmaceutically acceptable salt or solvate of each thereof to the patient, wherein the unit dose provides an average serum concentration of 50 ng/mL to 180 ng/mL, said concentration being sufficient to treat said addiction while maintaining a QT interval of less than about 500 ms during said treatment;
(b) monitoring the presence of noribogaine in the patient; and
(c) preventing exposure to methadone until all or substantially all of the noribogaine in the patient is removed.

22. A method of treating post-acute withdrawal in a patient in need thereof, comprising:
(a) administering a unit dose of noribogaine, an ester thereof, or a pharmaceutically acceptable salt or solvate of each thereof to the patient, wherein the unit dose provides an average serum concentration of 50 ng/mL to 180 ng/mL, said concentration being sufficient to treat post-acute withdrawal while maintaining a QT interval of less than about 500 ms during said treatment;
(b) monitoring the presence of noribogaine in the patient; and
(c) preventing exposure to methadone during the administration, wherein the unit dose is from 5% to 50% of a dose for treating the acute phase of addiction withdrawal.

23. The method of claim 22, wherein the unit dose is between about 3.5 mg and about 105 mg per day.

* * * * *